United States Patent
Bergo

(10) Patent No.: US 12,019,070 B2
(45) Date of Patent: Jun. 25, 2024

(54) BEAD-BASED ASSAYS FOR PROTEIN ANALYSIS

(71) Applicant: Adeptrix Corp., Beverly, MA (US)

(72) Inventor: Vladislav B. Bergo, Boston, MA (US)

(73) Assignee: ADEPTRIX CORP., Beverly, MA (US)

( * ) Notice: Subject to any disclaimer, the term of this patent is extended or adjusted under 35 U.S.C. 154(b) by 289 days.

(21) Appl. No.: 17/127,402

(22) Filed: Dec. 18, 2020

(65) Prior Publication Data

US 2021/0190773 A1 Jun. 24, 2021

Related U.S. Application Data

(60) Provisional application No. 62/950,676, filed on Dec. 19, 2019.

(51) Int. Cl.
*G01N 33/543* (2006.01)
*G01N 33/68* (2006.01)

(52) U.S. Cl.
CPC . *G01N 33/54306* (2013.01); *G01N 33/54313* (2013.01); *G01N 33/6845* (2013.01); *G01N 33/6848* (2013.01); *G01N 33/6878* (2013.01); *G01N 2440/00* (2013.01); *G01N 2570/00* (2013.01)

(58) Field of Classification Search
None
See application file for complete search history.

(56) References Cited

U.S. PATENT DOCUMENTS

| | | | |
|---|---|---|---|
| 9,618,520 B2 | 4/2017 | Bergo | |
| 10,101,336 B2 | 10/2018 | Bergo | |
| 10,451,631 B2 | 10/2019 | Bergo | |
| 11,131,674 B2 | 9/2021 | Bergo | |
| 11,391,729 B2 * | 7/2022 | Bergo | G01N 33/54306 |
| 2009/0270278 A1 | 10/2009 | Lim et al. | |
| 2010/0256015 A1 | 10/2010 | Lim et al. | |
| 2010/0317542 A1 | 12/2010 | Lim et al. | |
| 2011/0312897 A1 | 12/2011 | Allis et al. | |
| 2012/0077688 A1 | 3/2012 | Bergo et al. | |
| 2012/0202709 A1 | 8/2012 | Bergo | |
| 2014/0235471 A1 | 8/2014 | Bergo et al. | |
| 2014/0323330 A1 | 10/2014 | Bergo | |
| 2016/0008785 A1 | 1/2016 | Bergo | |
| 2017/0176453 A1 | 6/2017 | Bergo | |
| 2017/0219601 A1 | 8/2017 | Bergo | |
| 2019/0004038 A1 | 1/2019 | Bergo | |
| 2019/0072546 A1 | 3/2019 | Bergo | |
| 2021/0018513 A1 | 1/2021 | Bergo | |
| 2021/0389333 A1 | 12/2021 | Bergo | |

FOREIGN PATENT DOCUMENTS

| | | |
|---|---|---|
| WO | 2021127532 A1 | 6/2021 |
| WO | 2021127607 A1 | 6/2021 |

OTHER PUBLICATIONS

Qi et al., "The convergent chemical synthesis of histone H3 protein for site-specific acetylation at Lys56 and ubiquitination at Lys122," Chemical Communications, 53(29):4148-4151 (2017).
Ito et al., "Proteolytic Cleavage of High Mobility Group Box 1 Protein by Thrombin-Thrombomodulin Complexes," Arterioscler. Thromb. Vasc. Biol., 29:1825-1830 (2008).
International Search Report dated Mar. 16, 2021, for PCT Application No. PCT/US20/66275.
Written Opinion dated Mar. 16, 2021, for PCT Application No. PCT/US20/66275.
International Search Report dated Mar. 26, 2021, for PCT Application No. PCT/US20/66166.
Written Opinion dated Mar. 26, 2021, for PCT Application No. PCT/US20/66166.
Liu et al., "Clipping of arginine-methylated histone tails by JMJD5 and JMJD7," PNAS, 114(37):E7717-E7726 (2017).

* cited by examiner

*Primary Examiner* — Gary Counts
(74) *Attorney, Agent, or Firm* — KRIEGSMAN & KRIEGSMAN

(57) ABSTRACT

Bead-based assays for measuring protein biomarkers of proteolytic activity in biological systems are disclosed. In an embodiment, an assay involves incubating a sample containing multiple fragments of a naturally occurring protein with a bead array and subsequently analyzing individual reactive sites of the bead array by mass spectrometry.

9 Claims, 3 Drawing Sheets

Specification includes a Sequence Listing.

```
SEQUENCE LISTING

<160> NUMBER OF SEQ ID NOS: 41

<210> SEQ ID NO 1
<211> LENGTH: 19
<212> TYPE: PRT
<213> ORGANISM: Homo sapiens

<400> SEQUENCE: 1

Lys Ser Thr Gly Gly Lys Ala Pro Arg Lys Gln Leu Ala Thr Lys Ala
1               5                   10                  15

Ala Arg Lys

<210> SEQ ID NO 2
<211> LENGTH: 17
<212> TYPE: PRT
<213> ORGANISM: Homo sapiens

<400> SEQUENCE: 2

Ser Thr Gly Gly Lys Ala Pro Arg Lys Gln Leu Ala Thr Lys Ala Ala
1               5                   10                  15

Arg

<210> SEQ ID NO 3
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Acetylation

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr
            20

<210> SEQ ID NO 4
<211> LENGTH: 20
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Acetylation

<400> SEQUENCE: 4

Arg Thr Lys Gln Thr Ala Arg Lys Ser Thr Gly Gly Lys Ala Pro Arg
```

```
1               5                   10                  15

Lys Gln Leu Ala
            20

<210> SEQ ID NO 5
<211> LENGTH: 5
<212> TYPE: PRT
<213> ORGANISM: Homo sapiens

<400> SEQUENCE: 5

Ala Arg Thr Lys Gln
1               5

<210> SEQ ID NO 6
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Acetylation

<400> SEQUENCE: 6

Ala Arg Thr Lys Gln Thr Ala Arg Lys Ser Thr Gly Gly Lys Ala Pro
1               5                   10                  15

Arg Lys Gln Leu Ala Thr
            20

<210> SEQ ID NO 7
<211> LENGTH: 21
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Acetylation

<400> SEQUENCE: 7

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 8
<211> LENGTH: 27
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Trimethylation
<220> FEATURE:
<221> NAME/KEY: MOD_RES
<222> LOCATION: (16)..(16)
<223> OTHER INFORMATION: Methylation

<400> SEQUENCE: 8

Ala Thr Lys Ala Ala Arg Lys Ser Ala Pro Ala Thr Gly Gly Val Lys
1               5                   10                  15

Lys Pro His Arg Tyr Arg Pro Gly Thr Val Ala
            20                  25

<210> SEQ ID NO 9
<211> LENGTH: 25
<212> TYPE: PRT
<213> ORGANISM: Homo sapiens
```

```
<220> FEATURE:
<221> NAME/KEY: MOD_RES
<222> LOCATION: (6)..(6)
<223> OTHER INFORMATION: Trimethylation
<220> FEATURE:
<221> NAME/KEY: MOD_RES
<222> LOCATION: (15)..(15)
<223> OTHER INFORMATION: Methylation

<400> SEQUENCE: 9

Thr Lys Ala Ala Arg Lys Ser Ala Pro Ala Thr Gly Gly Val Lys Lys
1               5                   10                  15

Pro His Arg Tyr Arg Pro Gly Thr Val
            20                  25

<210> SEQ ID NO 10
<211> LENGTH: 29
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Acetylation
<220> FEATURE:
<221> NAME/KEY: MOD_RES
<222> LOCATION: (7)..(7)
<223> OTHER INFORMATION: Acetylation
<220> FEATURE:
<221> NAME/KEY: MOD_RES
<222> LOCATION: (16)..(16)
<223> OTHER INFORMATION: Dimethylation

<400> SEQUENCE: 10

Ala Thr Lys Ala Ala Arg Lys Ser Ala Pro Ser Thr Gly Gly Val Lys
1               5                   10                  15

Lys Pro His Arg Tyr Arg Pro Gly Thr Val Ala Leu Arg
            20                  25

<210> SEQ ID NO 11
<211> LENGTH: 27
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Acetylation
<220> FEATURE:
<221> NAME/KEY: MOD_RES
<222> LOCATION: (6)..(6)
<223> OTHER INFORMATION: Acetylation
<220> FEATURE:
<221> NAME/KEY: MOD_RES
<222> LOCATION: (15)..(15)
<223> OTHER INFORMATION: Dimethylation

<400> SEQUENCE: 11

Thr Lys Ala Ala Arg Lys Ser Ala Pro Ser Thr Gly Gly Val Lys Lys
1               5                   10                  15

Pro His Arg Tyr Arg Pro Gly Thr Val Ala Leu
            20                  25

<210> SEQ ID NO 12
<211> LENGTH: 17
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Methylation
<220> FEATURE:
```

```
<221> NAME/KEY: MOD_RES
<222> LOCATION: (8)..(8)
<223> OTHER INFORMATION: Acetylation
<220> FEATURE:
<221> NAME/KEY: MOD_RES
<222> LOCATION: (13)..(13)
<223> OTHER INFORMATION: Acetylation

<400> SEQUENCE: 12

Arg Thr Lys Gln Thr Ala Arg Lys Ser Thr Gly Gly Lys Ala Pro Arg
1               5                   10                  15

Lys

<210> SEQ ID NO 13
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Methylation
<220> FEATURE:
<221> NAME/KEY: MOD_RES
<222> LOCATION: (7)..(7)
<223> OTHER INFORMATION: Acetylation
<220> FEATURE:
<221> NAME/KEY: MOD_RES
<222> LOCATION: (12)..(12)
<223> OTHER INFORMATION: Acetylation

<400> SEQUENCE: 13

Thr Lys Gln Thr Ala Arg Lys Ser Thr Gly Gly Lys Ala Pro Arg
1               5                   10                  15

<210> SEQ ID NO 14
<211> LENGTH: 21
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Acetylation
<220> FEATURE:
<221> NAME/KEY: MOD_RES
<222> LOCATION: (16)..(16)
<223> OTHER INFORMATION: Citrullination

<400> SEQUENCE: 14

Arg Thr Lys Gln Thr Ala Arg Lys Ser Thr Gly Gly Lys Ala Pro Arg
1               5                   10                  15

Lys Gln Leu Ala Thr
            20

<210> SEQ ID NO 15
<211> LENGTH: 19
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Acetylation
<220> FEATURE:
<221> NAME/KEY: MOD_RES
<222> LOCATION: (15)..(15)
<223> OTHER INFORMATION: Citrullination

<400> SEQUENCE: 15

Thr Lys Gln Thr Ala Arg Lys Ser Thr Gly Gly Lys Ala Pro Arg Lys
1               5                   10                  15
```

Gln Leu Ala

```
<210> SEQ ID NO 16
<211> LENGTH: 14
<212> TYPE: PRT
<213> ORGANISM: Homo sapiens
<220> FEATURE:
<223> OTHER INFORMATION: N-term acetylation

<400> SEQUENCE: 16
```

Ala Val Pro Pro Thr Tyr Ala Asp Leu Gly Lys Ser Ala Arg
1               5                   10

```
<210> SEQ ID NO 17
<211> LENGTH: 17
<212> TYPE: PRT
<213> ORGANISM: Homo sapiens
<220> FEATURE:
<223> OTHER INFORMATION: N-term acetylation

<400> SEQUENCE: 17
```

Ala Val Pro Pro Thr Tyr Ala Asp Leu Gly Lys Ser Ala Arg Asp Val
1               5                   10                  15

Phe

```
<210> SEQ ID NO 18
<211> LENGTH: 26
<212> TYPE: PRT
<213> ORGANISM: Homo sapiens
<220> FEATURE:
<223> OTHER INFORMATION: N-term acetylation

<400> SEQUENCE: 18
```

Ala Val Pro Pro Thr Tyr Ala Asp Leu Gly Lys Ser Ala Arg Asp Val
1               5                   10                  15

Phe Thr Lys Gly Tyr Gly Phe Gly Leu Ile
            20                  25

```
<210> SEQ ID NO 19
<211> LENGTH: 11
<212> TYPE: PRT
<213> ORGANISM: Homo sapiens

<400> SEQUENCE: 19
```

Tyr Leu Arg Phe Ser Lys Glu Gln Leu Pro Ile
1               5                   10

```
<210> SEQ ID NO 20
<211> LENGTH: 16
<212> TYPE: PRT
<213> ORGANISM: Homo sapiens

<400> SEQUENCE: 20
```

His Pro Trp Asp Asp Ile Ser Tyr Val Leu Pro Glu His Met Ser Met
1               5                   10                  15

```
<210> SEQ ID NO 21
<211> LENGTH: 9
<212> TYPE: PRT
<213> ORGANISM: Homo sapiens

<400> SEQUENCE: 21
```

Ala Arg Thr Lys Gln Thr Ala Arg Lys
1               5

```
<210> SEQ ID NO 22
<211> LENGTH: 9
<212> TYPE: PRT
<213> ORGANISM: Homo sapiens

<400> SEQUENCE: 22

Leu Ala Thr Lys Ala Ala Arg Lys Ser
1               5

<210> SEQ ID NO 23
<211> LENGTH: 6
<212> TYPE: PRT
<213> ORGANISM: Homo sapiens

<400> SEQUENCE: 23

Gly Thr Val Ala Leu Arg
1               5

<210> SEQ ID NO 24
<211> LENGTH: 11
<212> TYPE: PRT
<213> ORGANISM: Homo sapiens

<400> SEQUENCE: 24

Ala Arg Thr Lys Gln Thr Ala Arg Lys Ser Thr
1               5                   10

<210> SEQ ID NO 25
<211> LENGTH: 4
<212> TYPE: PRT
<213> ORGANISM: Homo sapiens

<400> SEQUENCE: 25

Ala Arg Thr Lys
1

<210> SEQ ID NO 26
<211> LENGTH: 7
<212> TYPE: PRT
<213> ORGANISM: Homo sapiens

<400> SEQUENCE: 26

Lys Gln Leu Ala Thr Lys Ala
1               5

<210> SEQ ID NO 27
<211> LENGTH: 6
<212> TYPE: PRT
<213> ORGANISM: Homo sapiens

<400> SEQUENCE: 27

Gln Leu Ala Thr Lys Ala
1               5

<210> SEQ ID NO 28
<211> LENGTH: 10
<212> TYPE: PRT
<213> ORGANISM: Homo sapiens

<400> SEQUENCE: 28

Arg Thr Lys Gln Thr Ala Arg Lys Ser Thr
1               5                   10

<210> SEQ ID NO 29
```

```
<211> LENGTH: 6
<212> TYPE: PRT
<213> ORGANISM: Homo sapiens

<400> SEQUENCE: 29

Lys Gln Leu Ala Thr Lys
1               5

<210> SEQ ID NO 30
<211> LENGTH: 9
<212> TYPE: PRT
<213> ORGANISM: Homo sapiens

<400> SEQUENCE: 30

Thr Lys Gln Thr Ala Arg Lys Ser Thr
1               5

<210> SEQ ID NO 31
<211> LENGTH: 5
<212> TYPE: PRT
<213> ORGANISM: Homo sapiens

<400> SEQUENCE: 31

Lys Gln Leu Ala Thr
1               5

<210> SEQ ID NO 32
<211> LENGTH: 5
<212> TYPE: PRT
<213> ORGANISM: Homo sapiens

<400> SEQUENCE: 32

Leu Ala Thr Lys Ala
1               5

<210> SEQ ID NO 33
<211> LENGTH: 4
<212> TYPE: PRT
<213> ORGANISM: Homo sapiens

<400> SEQUENCE: 33

Lys Gln Leu Ala
1

<210> SEQ ID NO 34
<211> LENGTH: 4
<212> TYPE: PRT
<213> ORGANISM: Homo sapiens

<400> SEQUENCE: 34

Ala Thr Lys Ala
1

<210> SEQ ID NO 35
<211> LENGTH: 22
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Acetylation
<220> FEATURE:
<221> NAME/KEY: MOD_RES
<222> LOCATION: (17)..(17)
<223> OTHER INFORMATION: Citrullination

<400> SEQUENCE: 35
```

Ala Arg Thr Lys Gln Thr Ala Arg Lys Ser Thr Gly Gly Lys Ala Pro
1               5                   10                  15

Arg Lys Gln Leu Ala Thr
            20

<210> SEQ ID NO 36
<211> LENGTH: 21
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Acetylation
<220> FEATURE:
<221> NAME/KEY: MOD_RES
<222> LOCATION: (17)..(17)
<223> OTHER INFORMATION: Citrullination

<400> SEQUENCE: 36

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 37
<211> LENGTH: 22
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Citrullination
<220> FEATURE:
<221> NAME/KEY: MOD_RES
<222> LOCATION: (9)..(9)
<223> OTHER INFORMATION: Acetylation

<400> SEQUENCE: 37

Ala Arg Thr Lys Gln Thr Ala Arg Lys Ser Thr Gly Gly Lys Ala Pro
1               5                   10                  15

Arg Lys Gln Leu Ala Thr
            20

<210> SEQ ID NO 38
<211> LENGTH: 21
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Citrullination
<220> FEATURE:
<221> NAME/KEY: MOD_RES
<222> LOCATION: (9)..(9)
<223> OTHER INFORMATION: Acetylation

<400> SEQUENCE: 38

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 39
<211> LENGTH: 22
<212> TYPE: PRT
<213> ORGANISM: Homo sapiens
<220> FEATURE:

```
<221> NAME/KEY: MOD_RES
<222> LOCATION: (2)..(2)
<223> OTHER INFORMATION: Citrullination
<220> FEATURE:
<221> NAME/KEY: MOD_RES
<222> LOCATION: (9)..(9)
<223> OTHER INFORMATION: Acetylation
<220> FEATURE:
<221> NAME/KEY: MOD_RES
<222> LOCATION: (17)..(17)
<223> OTHER INFORMATION: Citrullination

<400> SEQUENCE: 39

Ala Arg Thr Lys Gln Thr Ala Arg Lys Ser Thr Gly Gly Lys Ala Pro
1               5                   10                  15

Arg Lys Gln Leu Ala Thr
            20

<210> SEQ ID NO 40
<211> LENGTH: 21
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Citrullination
<220> FEATURE:
<221> NAME/KEY: MOD_RES
<222> LOCATION: (9)..(9)
<223> OTHER INFORMATION: Acetylation
<220> FEATURE:
<221> NAME/KEY: MOD_RES
<222> LOCATION: (17)..(17)
<223> OTHER INFORMATION: Citrullination

<400> SEQUENCE: 40

Ala Arg Thr Lys Gln Thr Ala Arg Lys Ser Thr Gly Gly Lys Ala Pro
1               5                   10                  15

Arg Lys Gln Leu Ala
            20

<210> SEQ ID NO 41
<211> LENGTH: 9
<212> TYPE: PRT
<213> ORGANISM: Homo sapiens

<400> SEQUENCE: 41

Ala Thr Lys Ala Ala Arg Lys Ser Ala
1               5
```

BEAD-BASED ASSAYS FOR PROTEIN ANALYSIS

RELATED APPLICATIONS

The present application claims the benefit under 35 U.S.C. 119(e) of U.S. Provisional Patent Application No. 62/950,676, inventor Vladislav B. Bergo, filed Dec. 19, 2019, the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Dec. 16, 2020, is named 84293A_SL.txt and is 10,724 bytes in size.

FIELD

The embodiments disclosed herein relate generally to bead-based assays and more specifically to measuring analytes in biological samples using bead-based assays. The embodiments disclosed herein also relate to proteomics, epigenetics, protein quantification, post-translational modifications of proteins, analysis of histones, affinity separations, microarrays and mass spectrometry.

BACKGROUND

Detection, identification and quantification of analytes in biological samples is an important area of biology, pharmacology and medicine. In many applications the analytes are proteins and/or protein fragments, such as proteolytic peptides produced by enzymatic digestion of precursor proteins. Mass spectrometry (MS) is the key analytical platform for analyzing proteins and peptides.

Various bead-based MS methods for multiplexed analysis of proteins and peptides are described in the U.S. Pat. No. 9,618,520, U.S. patent application Ser. No. 13/369,939, Publication No. US 2012-0202709 A1 and other publications.

However, the published methods do not describe using multiplexed bead-based assays for targeted analysis of endogenous proteolytic activity or epigenetic profiling.

Accordingly, it is desirable to provide methods and compositions that will enable screening of distinct proteins and peptides by MS in a bead array format.

SUMMARY

In one aspect, the present specification describes methods of performing protein screening using singleplex or multiplexed affinity capture on a bead array followed by MS analysis of the bead array. Some of the described methods include measuring diseased and normal samples using a multiplexed bead-based assay and detecting protein fragments that are specifically cleaved by an endogenous protease.

In another aspect, the present specification describes a bead array, in which a reactive site contains a capture agent that specifically recognizes and specifically binds multiple fragments of a naturally occurring precursor protein.

In yet another aspect, the present specification describes a bead array, in which a reactive site contains a capture agent that specifically recognizes a post-translationally modified (PTM) site within a histone. The reactive site is capable of specifically binding multiple fragments of the histone that form an N-terminal or a C-terminal peptide ladder. Distinct reactive sites of the bead array recognize distinct peptide ladders.

In yet another aspect, the present specification describes a method of measuring abundance of a protein analyte in a sample. The method includes the steps of capturing at least two fragments of a precursor protein on a reactive site of a bead array, measuring intensities of signals from the captured fragments in a mass spectrum and using solely the intensities of the signals to determine an abundance of the precursor protein in the sample.

In yet another aspect, the present specification describes a method of analyzing a sample by capturing multiple fragments of a precursor protein on a reactive site of a bead array and measuring signals from the individual fragments with a coefficient of variation (CV) below 50%.

The methods and compositions described in this specification may be utilized to analyze various biological samples, including cell-free protein transcription-translation reactions, bacterial cells, mammalian cells, cell culture supernatants, animal models, xenografts, tissue biopsies, biofluids such as serum, plasma and cerebrospinal fluid, and others. The described methods and compositions may be utilized in a broad range of applications including basic research, pharmaceutical drug discovery and drug development, disease diagnostics and prognostics, biomarker discovery and validation, personalized medicine, precision medicine, systems biology and others.

DESCRIPTION OF FIGURES

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A discloses SEQ ID NOS 21-23, respectively, in order of appearance.

FIG. 2B discloses SEQ ID NOS 24-28, 25, 29, 27, 30, 25, 31-32, 25, and 33-34, respectively, in order of appearance.

FIG. 4B discloses SEQ ID NO: 6 (with terminal residue) and SEQ ID NO: 7 (without terminal residue).

FIG. 10A discloses SEQ ID NOS 35 and 14 (with terminal residues) and SEQ ID NOS 36 and 15 (without terminal residues), respectively, in order of appearance.

FIG. 10C discloses SEQ ID NOS 37, 35, 39 and 6 (with terminal residue) and SEQ ID NOS 38, 36, 40, and 7 (without terminal residue), respectively, in order of appearance.

DETAILED DESCRIPTION

Figure 1:
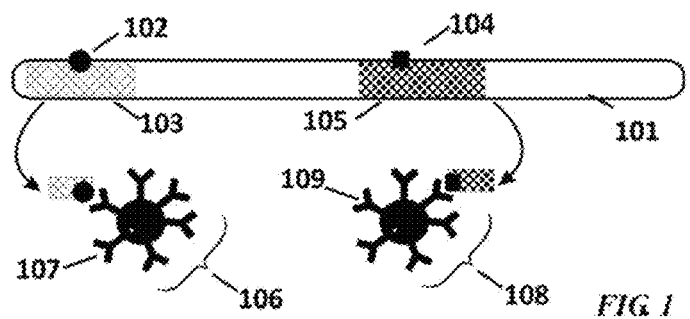
FIG. 1 schematically depicts a bead array and a method of binding fragments of a protein to distinct reactive sites of the bead array.

The term "bead array" refers to a group that includes at least two reactive sites. A bead array may be located in a container, such as a microcentrifuge tube, or in a well of a multi-well plate, in which case it may be referred to as a suspension bead array.

The term "reactive site" refers to a combination of a bead and at least one capture agent that is associated with the bead.

The term "capture agent" refers to a molecule or a molecular complex that is capable of binding a compound. A singular form of the term "capture agent" may refer to a plurality of identical molecules or a plurality of identical molecular complexes. For example, it may refer to a plurality of identical antibody molecules.

The terms "target analyte" and "target" are used interchangeably throughout the instant specification and generally refer to a binding partner of a capture agent. Singular forms of the terms "target analyte" and "target" may refer to a plurality of molecules, e.g. a plurality of peptide molecules.

The terms "peptide" and "polypeptide" are used interchangeably throughout the specification and refer to a molecule containing at least two amino acids that are linked by an amide bond, which is also known as a peptide bond.

The term "protein" is used according to its definition in the fields of biochemistry and molecular biology.

The terms "well" and "microwell" are used interchangeably throughout the instant specification and refer to a topological feature such as a pit or a depression that is able to hold a liquid medium, a particle or both.

The term "microarray" refers to a plurality of spatially separated spots that are positioned on a substantially flat surface of a solid support. Individual spots within a microarray may contain a matrix for mass spectrometry.

The term "histone" refers to a human or a non-human protein that belongs to one of the histone families: H1/H5, H2A, H2B, H3, H4. An example of a human histone protein is histone H3.1, which is a sequence variant of histone H3. It is a product of the gene H3C1. The entry number and the entry name for human histone H3.1 in the Universal Protein resource (UniProt) database is P68431 and H31 HUMAN, respectively.

The term "histone H3" refers to at least one of sequence variants of histone H3, such as histone H3.1 (UniProt entry number P68431), histone H3.1t (UniProt entry number Q16695), histone H3.2 (UniProt entry number Q71DI3), histone H3.3 (UniProt entry number P84243), histone H3.3C (UniProt entry number Q6NXT2).

The term "histone tail" refers to an N-terminal portion of a histone, such as histone H3 or histone H4. A histone tail typically contains less than 100 amino acids and includes one or several PTM sites.

The terms "clipped histone tail" and "clipped tail of a histone" refer to a peptide that has been cleaved ("clipped") from an N-terminal portion of a histone via a proteolytic process known as histone tail clipping. Histone tail clipping is a well-documented event that occurs in human and non-human cells.

The term "clipped histone" refers to a histone that lacks at least a fragment of a histone tail. An example of a clipped histone is human histone H3.1 containing a sequence that starts at Thr22. As histone tail clipping occurs at various sites, a clipped histone may still possess a histone tail, however such histone tail will be shorter compared to a histone tail in a non-clipped histone.

The terms "non-clipped histone" and "intact histone" refer to a histone that contains an intact histone tail. An example of a non-clipped histone is human histone H3.1 containing a sequence that starts at Ala1 and terminates at Ala135. Note that a sequence of a histone typically starts with a residue that immediately follows an N-terminal methionine.

The term "transcription factor" refers to a protein that is capable of binding to DNA in a sequence-specific manner. A transcription factor contains at least one DNA-binding domain. There are over 1,000 known transcription factors in the human genome.

The term "ion channel" refers to a membrane protein that is capable of forming a pore, which allows small molecules and/or ions to pass through, usually in response to an electrochemical gradient.

The term "PTM site" refers to a post-translationally modified site in a protein or in a polypeptide.

In an embodiment, the instant specification describes a bead array containing a reactive site, i.e. a bead and a capture agent associated with the bead. The capture agent specifically recognizes and specifically binds multiple fragments of a naturally occurring protein, such as histone. The protein may be either of human or non-human origin. The protein may be found in multiple organs, tissues and/or biofluids. The bead array also contains a decoding combination. The decoding combination contains information about molecular weights of the multiple fragments that are recognized by the capture agent. In an embodiment, the decoding combination also contains information about a presence of the multiple fragments in a same sample, for example in a sample produced by digesting a biological material using a specific protease. In an embodiment, the decoding combination further contains information about at least one of the multiple fragments, e.g. peptides containing a terminus that is cleaved by an endogenous protease.

The quantity of the protein fragments that are specifically recognized by the capture agent may be at least 2, at least 3, at least 4, at least 5, at least 6, at least 7, at least 8, at least 9, at least 10, greater than 10, greater than 15, greater than 20, greater than 25, greater than 30, greater than 40, greater than 50 or greater than 60.

The capture agent may be configured to specifically recognize distinct fragments of the protein that differ by a length of a single terminal amino acid, a so-called peptide ladder. For example, the distinct fragments may contain 10, 11, 12, 13, 14, 15 and 16 amino acid residues. The use of such capture agent enables analysis of an exoproteolytic activity.

The multiple fragments (peptides) may be produced by digesting the protein with a protease ("an external protease"). The protein may be purified prior to being digested. Alternatively, the protein may be digested directly in a sample, e.g. directly in a cell or a tissue lysate or a biofluid without performing prior purification or enrichment. Individual fragments (peptides) may contain a site (a terminus), such as an N-terminus or a C-terminus that is specifically cleaved by the external protease, as well as a site that is not specifically cleaved by the external protease (a non-specifically cleaved site) and also a variable number of internal proteolytic cleavage sites that are recognized but not cleaved by the protease. The external protease may be one of the proteolytic enzymes that are commonly used in proteomics, namely trypsin, chymotrypsin, ArgC, LysC, LysN, GluC, AspN, ProC, thermolysin, elastase or pepsin. Proteolytic cleavage sites that are recognized by each of these enzymes are well known. For example, sequencing grade trypsin is known to recognize and cleave sites Lys-X and Arg-X where X is any amino acid other than proline, while sequencing grade Lys-C is known to recognize and cleave sites Lys-X where X is any amino acid including proline. Endoproteinase ArgC (clostripain) is known to recognize and cleave predominantly sites Arg-X and to a lesser extent Lys-X, where X is any amino acid other than proline. A specifically cleaved site is a site that has been recognized by a particular protease and cleaved by the protease. A non-specifically cleaved site is a site that has been produced via a mechanism other than specific cleavage by the protease, for example such site may be produced via cleavage by a distinct protease that is endogenous to a cell, a tissue or a biofluid from which the protein is derived ("an endogenous protease"). Examples of non-specifically cleaved sites in a peptide that was produced by digesting a protein with sequencing grade trypsin are the peptide C-terminus that contains an amino acid other than Lys or Arg and the peptide N-terminus that contains an amino acid that is not preceded by Lys or Arg in the sequence of the precursor protein. A missed cleavage site is a proteolytic cleavage site that is recognized by the protease and has not been cleaved by the protease. An example of a missed cleavage site is an internal lysine in a peptide that was produced by digesting a protein with sequencing grade Lys-C. The capture agent may be configured to specifically recognize and bind both a fragment that contains a site specifically cleaved by the external protease and a fragment that contains a site specifically cleaved by the endogenous protease. The fragment may further contain an internal (i.e. not a terminal) cleavage site that is recognized by the external protease.

A non-specifically cleaved site may be generated not by an endogenous protease but as a product of premature termination of RNA transcription, premature termination of protein translation, or both, either in cell or by in-vitro transcription-translation reaction.

Multiple fragments containing variable numbers of proteolytic cleavage sites may be generated by varying reaction parameters such as the enzyme to protein substrate ratio, temperature, duration of the digestion reaction and possibly others.

Multiple fragments may contain a variable number of PTM sites, namely sites that are phosphorylated, acetylated, mono-, di-, or tri-methylated, ubiquitinated, succinylated, oxidized, dehydrated or contain other modifications. Some fragments may contain more than one PTM type, e.g. acetylation and methylation may exist within a same sequence.

There are several potential benefits of using a capture agent that recognizes multiple fragments of a protein. These benefits include using a same bead array to analyze samples prepared using different proteases or different digestion conditions, greater confidence in the target analyte identification and the ability to detect novel modifications and PTM sites including protein sites that are cleaved by an endogenous protease. A capture agent that recognizes multiple fragments of a human protein is also likely to recognize fragments of a homologous protein from a different species, e.g. mouse.

A capture agent may be a commercially available antibody or an aptamer that has been validated for recognizing multiple fragments of a protein. The validation is achieved by performing a series of incubations of bead arrays containing the capture agent with samples containing the protein of interest that have been digested using different digestive enzymes, different combinations of digestive enzymes, different conditions of digestion reactions, etc and then detecting the captured fragments using MS. Examples of validating commercially available antibodies using this method are included in the specification.

A capture agent, e.g. an antibody may be also specifically created to recognize multiple fragments of a precursor protein. Custom designed antibodies are available from various vendors. For example, synthetic combinatorial recombinant antibody production service HUCAL® is offered by Bio-Rad (Hercules CA).

Bead arrays described in this specification may be used for performing epigenetics analysis, e.g. for analyzing one or several PTM sites within one or several histones. As schematically depicted in FIG. 1, a multiplexed bead array may be assembled to contain at least two reactive sites such that the first reactive site 106 contains a capture agent 107 that specifically recognizes a first PTM site 102 within a fragment 103 of a histone 101 and the second reactive site 108 contains a distinct capture agent 109 that specifically recognizes a second PTM site 104 within a same or a different fragment 105 of the histone 101. The two PTM sites may contain different modifications of a same type of an amino acid, for example an acetylated lysine and a mono-, di-, or trimethylated lysine. The two PTM sites may contain different types of amino acids, for example a lysine and a serine or a threonine. A position of the first PTM site may coincide with a position of the second PTM site. Alternatively, a position of the first PTM site may be adjacent to a position of the second PTM site.

Because the capture agents of the two reactive sites recognize different PTM sites, they may recognize different fragments of the histone, depending upon localizations of the PTM sites in a sequence of the histone and the protease specificity. Such different fragments may be overlapping, non-overlapping or adjacent to each other. The first capture agent may be configured to recognize a fragment that occurs in a greater number of sequence variants of the histone while the second capture agent may be configured to recognize a fragment that occurs in a smaller number of sequence variants of the histone. Configuring the capture agents to recognize adjacent fragments in a sequence of a protein allows comprehensive analysis of at least a portion of the sequence of the protein without gaps in the sequence coverage.

One or several capture agents included in the bead array may be configured to specifically recognize a PTM site in a fragment of the histone that contains a specifically cleaved protease recognition site and also in a fragment of the histone that contains a non-specifically cleaved site, e.g. a site that is cleaved by an endogenous protease. Capturing non-specifically cleaved histone fragments from a proteolytically digested sample enables detection of an endogenous proteolytic activity that causes a removal of an N-terminal fragment from the histone, which is known as histone tail clipping. An example of the histone tail clipping is a well-documented cleavage of the Ala21-Thr22 chemical bond by cathepsin L in histone H3. Several capture agents may be included in the bead array that individually recognize non-specifically cleaved fragments that are adjacent to each other in a sequence of the histone. For example, there may be included a capture agent that recognizes a fragment of histone H3 containing Ala21 at that fragment's C-terminus and a distinct capture agent that recognizes a fragment of histone H3 containing Thr22 at that fragment's N-terminus. Utilizing multiple capture agents that independently recognize adjacent fragments in a sequence of the protein helps to ensure that there are no gaps in the sequence coverage of the protein, in this case histone H3.

In the above example, fragments of histone H3 containing Ala21 at the C-terminus and fragments containing Thr22 at the N-terminus may be recognized as non-specifically cleaved fragments, i.e. fragments that do not contain a specifically cleaved site at the C-terminus or at the N-terminus, respectively, if the histone was digested using a protease such as trypsin, chymotrypsin, ArgC, LysC, LysN, GluC, AspN, ProC, or pepsin. On the other hand, such fragments may be produced via specific cleavage by thermolysin or elastase that are known to specifically cleave Ala-X bonds.

One or several capture agents included in the bead array may be configured to specifically recognize a PTM site only if that PTM site is not adjacent to another PTM site. For example, adjacent Lys9 and Ser10 in the sequence of histone H3 are known PTM sites. A capture agent, e.g. an antibody may be included in the bead array that specifically recognizes a proteolytic fragment of histone H3 only if the fragment contains a phosphorylated Ser10 (H3S10ph) that is adjacent to a non-acetylated and non-methylated Lys9.

One or several capture agents included in the bead array may be configured to specifically recognize a PTM site only if that PTM site is adjacent to another PTM site. A capture agent, e.g. an antibody may be included in the bead array that specifically recognizes a proteolytic fragment of histone H3 only if the fragment contains a phosphorylated Ser10 (H3S10Ph) that is adjacent to: (1) an acetylated Lys9 (H3K9ac), (2) a mono-, di- or tri-methylated Lys9 (H3K9me1, H3K9me2, H3K9me3), or (3) either a methylated or acetylated Lys9.

One or several capture agents included in the bead array may be configured to specifically recognize more than one distinct PTM sites within a sequence of a histone. For example, an antibody may recognize both di- and tri-methylated Lys27 in histone H3 (H3K27me2 and H3K27me3). A distinct capture agent may then be included in the bead array that specifically recognizes a distinct PTM site at the same position, e.g. at Lys27 in histone H3. For example, the bead array may also contain an antibody that recognizes mono-methylated Lys27 (H3K27me1), an antibody that recognizes ubiquitinated Lys27 (H3K27ub) in histone H3 or both the H3K27me1 and H3K27ub antibodies.

The bead array may contain a capture agent that specifically recognizes a non-PTM site within the histone, for example a non-modified lysine. Furthermore, the bead array may contain a capture agent that specifically recognizes a fragment of a protein other than the histone.

Histones are known to be extensively modified at multiple sites. Accordingly, the bead array may contain a capture agent that is verified to specifically recognize a particular PTM site in at least 10, at least 20, at least 30, at least 40, at least 50 or at least 60 distinct fragments of the histone, the distinct fragments having distinct patterns of PTM sites. Having such capture agent in the bead array enables highly multiplexed analysis, e.g. at least 10-plex, at least 20-plex, at least 30-plex, at least 40-plex, at least 50-plex or at least 60-plex to be performed from a single reactive site. Examples of assays that capture at least 10 distinct histone fragments that have molecular weights that are spaced apart by at least 14 Da are provided in the specification. Because all fragments captured by the same reactive site have similar chemical sequence as they are derived from a same region of a same protein, their ionization properties in MALDI MS are also similar. Specifically, at least 5, at least 10, at least 20, at least 30, at least 40, or at least 50 distinct fragments of the protein that are captured on a single reactive site may have greater than 50%, greater than 60%, greater than 70%, greater than 80%, greater than 85%, greater than 90% or greater than 95% sequence identity. Capturing multiple distinct peptides that have nearly identical or at least very similar chemical sequence on a same reactive site enables various quantitative applications that may not require the use of synthetic peptide standards.

Figure 2A:
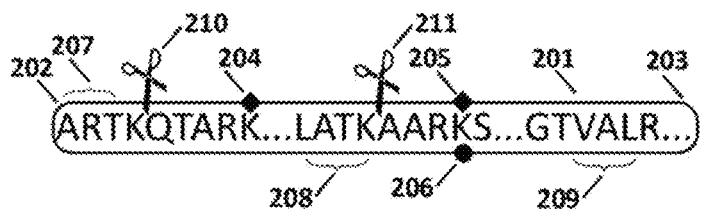
FIG. 2A schematically depicts a histone sequence that contains several PTM sites and protease cleavage sites.

FIG. 2A schematically depicts a histone sequence 201 that contains an N-terminus 202 and a C-terminus 203. The sequence contains several PTM sites 204, 205 and 206. Distinct PTM sites, e.g. sites 204 and 205 may contain an identical modification such as acetylated lysine. A same residue in the sequence may be a site of distinct modifications, e.g. sites 205 and 206 may contain an acetylated and a tri-methylated lysine, respectively. In addition to the PTM sites containing reversible modifications, the sequence may contain histone tail clippings sites 207, 208 and 209 that are recognized by an endogenous protease, which is active in a cell, a tissue or a biofluid from which the histone is derived. An example of an endogenous protease is cathepsin L. The histone tail clipping may occur at adjacent residues, e.g. residues within sites 207 and 208 or at non-adjacent residues, e.g. residues within site 209. The histone tail clipping sites may be located at the N-terminus, such as site 207 or at some distance from the N-terminus, such as sites 208 and 209. Also depicted in FIG. 2A are sites 210 and 211 that are recognized and cleaved by proteolytic enzymes, such as trypsin, ArgC, LysC and/or others.

Figure 2B:
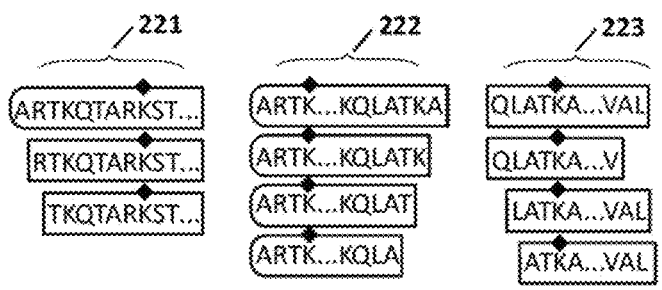
FIG. 2B schematically depicts peptide ladders formed by fragments of a histone that contain sequentially cleaved amino acids.

If histone tail clipping occurs at adjacent residues, a peptide ladder containing peptides that differ in a single amino acid may be generated. As schematically depicted in FIG. 2B, a peptide ladder 221 may be generated by removing residues from an N-terminus of a peptide that itself is a fragment of the histone. A peptide ladder 222 may be generated by removing residues from a C-terminus of a peptide that is a fragment of the histone. A peptide ladder 223 may be generated by removing residues from both an N-terminus and a C-terminus of a peptide that is a fragment of the histone, with removal of adjacent residues occurring on either end or on both ends. Note that the peptides in group 223 contain both an N-terminus and a C-terminus that are produced via histone tail clipping by an endogenous protease or proteases.

After an endogenous protease cleaves an N-terminal fragment (tail), both the tail and the clipped histone remain in the sample, e.g. in a cell or in a tissue and are accessible for affinity enrichment. If the sample is digested using a proteolytic enzyme, such as LysC, fragments of the clipped and non-clipped histones may be detectable in the sample.

Various groups of histone fragments may be present in a biological sample and available for affinity capture after the histone tail clipping occurs and the sample is digested using a proteolytic enzyme. One example is a mixture that contains cleaved histone tails but does not include proteolytic fragments of the C-terminal portion of the clipped histone. Peptides in such mixture may be captured on a reactive site that contains an antibody that specifically recognizes a PTM site that is present in the cleaved histone tails. Another example is a mixture that contains both cleaved histone tails and proteolytic fragments of the C-terminal portion of the clipped histone. Even though both the cleaved histone tails and the fragments of the clipped histone are captured on a same reactive site, they may be distinguished by their MW and/or MS-MS fragmentation profile. Yet another example is a mixture of proteolytic fragments derived from the C-terminal portion of the clipped histone that does not contain cleaved histone tails. Peptides in such mixture may contain one or several missed proteolytic cleavage sites that are recognized but not cleaved by the proteolytic enzyme. Such mixture may also include peptides that are proteolytic fragments of an intact histone.

The bead arrays described in this specification may be used in various applications including quantitative measurements of protein abundance and/or protein modifications in a biological sample. Some of these applications are described below and in the Examples section of the specification.

In an embodiment, the instant specification describes a method for characterizing a protein in a sample. The protein-containing sample is digested with a protease that cleaves the protein at a first site and at a second site to generate a digested sample, which contains a first protein fragment and a second protein fragment, respectively. A rate of the protein cleavage by the protease at the first site may be different from a rate of the protein cleavage at the second site. The digested sample is then incubated with a reactive site of a bead array that contains a capture agent that specifically recognizes the first and the second fragments. During the incubation, the first and the second fragments specifically bind to the reactive site of the bead array. The reactive site is then individually analyzed by MS such that the measured mass spectrum contains signals from the first and the second fragments. These signals are identified in the mass spectrum and their intensity values are used to determine abundance of the precursor protein in the sample.

In an embodiment, the sample also contains a third fragment of the protein that is not produced by specific cleavage of the protein by the protease. For example, the third fragment may be produced via cleavage of the protein by an endogenous proteolytic enzyme that is active in a biological cell, tissue or a biofluid from which the sample is derived. Alternatively, it may be produced by premature termination of protein synthesis on the ribosome. The third fragment may contain one or more than one internal cleavage sites that are recognized by the protease. The third fragment is captured on the reactive site along with the first and the second fragments, detected by MS and an intensity value of a signal from the third fragment is used in addition to the signals from the first and second fragments to determine abundance of the protein in the sample.

The bead array may contain replicates of the reactive site, all replicates containing the capture agent. If the replicates are included in the bead array the first and the second fragments will bind to the replicate sites. Using methods described in the Examples section it is possible to obtain mass spectra individually from the replicates of the reactive site and detect signals from at least the first fragment in the mass spectra with a low coefficient of variation (CV) of less than 50%, less than 40%, less than 30%, less than 20%, less than 10% or less then 5%.

The methods described in this specification may be applied to perform epigenetic analysis. In an embodiment, the epigenetic analysis is performed on a sample that contains at least a first fragment and a second fragment of a histone, the first fragment contains a first PTM site and a distinct second PTM site while the second fragment also contains the first PTM site and a third PTM site that is distinct from the first and the second PTM sites. The sample is incubated with a bead array that contains a reactive site that contains a capture agent that specifically recognizes the first PTM site causing the first and the second fragments to specifically bind to the reactive site. After the incubation the reactive site is individually analyzed by MS to obtain a mass spectrum that contains signals from the first and the second fragments. The intensities of the signals from the first and the second fragments are used to determine abundance of the second PTM site in the histone.

The sample may also contain more than 2 distinct histone fragments, e.g. at least 10 fragments, each of these fragments containing the first PTM site and having a distinct overall pattern of PTM sites. Each fragment specifically binds to the reactive site and a signal from each fragment is measured by individually analyzing the reactive site by MS with a CV of less than 50%, less than 10%, or less than 5%.

In an embodiment, the sample contains multiple distinct fragments of a histone, e.g. at least a first fragment and a second fragment of a histone, the first fragment contains a first PTM site, the second fragment contains a second PTM site. In an embodiment, the first fragment is identical to the second fragment. Alternatively, a sequence of the first fragment is adjacent to a sequence of the second fragment. In an embodiment, each of the first and the second fragments contains a site that has been specifically cleaved by a protease and a site that has not been specifically cleaved by the protease. In an embodiment, each of the first and the second fragments contains a site that has been specifically cleaved by a first protease and a site that has been specifically cleaved by a distinct second protease. In an embodiment, the first fragment is derived from a greater number of sequence variants of the histone than the second fragment. The bead array contains a first reactive site and a second reactive site, each of the reactive sites containing a distinct capture agent that specifically recognizes a distinct PTM site in the histone. Incubation of the sample with the bead array causes specific binding of the first fragment to the first reactive site and of the second to the second reactive site. Each of the reactive sites is individually analyzed using MS, signals from the first and the second fragments are detected and abundances of the first and the second PTM sites are determined using intensity values of the detected signals.

The method described above may include capturing more than one distinct fragment of a histone on a single reactive site. For example, if the first fragment contains an acetylated lysine, e.g. H3K9ac, fragments of the histone that contain mono-, di- and trimethylated lysines in nearby positions, e.g. H3K4me2, H3K14me3, H3K18me1 may also specifically bind to the first reactive site.

In an embodiment, the sample contains a first fragment and a second fragment of the histone, the first fragment contains a first PTM site and a second PTM site, the second fragment contains the first PTM site and a third PTM site, the bead array contains a reactive site that contains a capture agent that specifically recognizes the first PTM site. The sample is contacted with the bead array causing the first and the second fragments to specifically bind to the reactive site. Signals from the first and the second fragments are detected in a mass spectrum that is obtained by individually analyzing the reactive site using MS and abundances of the second and third PTM sites in the histone are determined using solely intensity values of the detected signals.

In an embodiment, the sample contains at least 10 distinct fragments of the histone and the method includes specifically binding each of the fragments to the reactive site and detecting signals from each distinct fragment by individually analyzing the reactive site using mass spectrometry.

Because of a major role that histones play in transcriptional regulation, alterations of their activity detected via analysis of post-translational modifications may be correlated with changes in one or several biological pathways that are involved in emergence and/or progression of various human diseases. The disclosed methods and assays enable detection of altered patterns of histone modifications in a human brain tissue that correlate with an occurrence of a neurological disease, namely Alzheimer's disease. More generally, the disclosed methods and assays may be used for analysis of various biological tissues and studies of a wide range of human and non-human diseases.

The methods disclosed in the instant specification allow direct enrichment of histone fragments from biological samples without performing nucleosome isolation, acid extraction or salt extraction. The direct enrichment methods have sufficient sensitivity to detect even lower abundance individual histone PTM sites and combinations of PTM sites. The direct enrichment methods also offer the benefit of capturing cleaved histone tails, which may not be accessible via conventional methods of histone fractionation.

An alternative workflow is also possible in which a sample is subjected to histone enrichment using nucleosome isolation, acid-based histone extraction or salt-based histone extraction followed by affinity capture of histone fragments using a bead array containing histone-specific antibodies. An unreacted portion of the sample is then subjected to affinity capture to enrich the fraction of cleaved histone tails.

In an embodiment, the specification discloses a method for characterizing a protein, which comprises the steps of: (1) obtaining a sample produced by digesting a biological material using an external protease, the sample containing a first peptide and a second peptide, the first and the second peptides being distinct proteolytic fragments of a naturally occurring protein, the first peptide containing a terminus cleaved by an endogenous protease, the second peptide containing a terminus cleaved by the external protease; (2) causing the first and the second peptides to specifically bind to a reactive site, the reactive site comprising a bead and a capture agent associated with the bead; (3) individually analyzing the reactive site to obtain a mass spectrum that contains a signal from the first peptide and a signal from the second peptide and (4) determining an abundance of the first peptide by analyzing the signal from the first peptide and the signal from the second peptide.

In an embodiment, the specification discloses a method for characterizing a protein, which comprises the steps of: (1) obtaining a sample produced by digesting a biological material using an external protease, the sample containing a first peptide and a second peptide, the first and the second peptides being distinct proteolytic fragments of a naturally occurring protein, each of the first and the second peptides containing both an N-terminus and a C-terminus cleaved by an endogenous protease and not by the external protease; (2) causing the first and the second peptides to specifically bind to a reactive site, the reactive site comprising a bead and a capture reagent associated with the bead; (3) individually analyzing the reactive site to obtain a mass spectrum that contains a signal from the first peptide and a signal from the second peptide and (4) determining an abundance of the first peptide by analyzing the signal from the first peptide and optionally the signal from the second peptide.

In an embodiment, the specification discloses a bead array that includes a reactive site and a decoding combination, the reactive site comprises a bead and a capture agent, the capture agent specifically recognizes a first peptide and a second peptide, the first and the second peptides are distinct proteolytic fragments of a naturally occurring protein, the first peptide contains a terminus cleaved by an endogenous protease, the second peptide contains a terminus cleaved by an external protease, the decoding combination contains information about a molecular weight of the first peptide, a molecular weight of the second peptide, and a presence of both the first and the second peptides in a sample produced by digesting the protein using the external protease.

The present disclosure is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the present disclosure, and are not intended to limit the scope of the present disclosure nor are they intended to represent that the experiments below are all or the only experiments performed. Efforts have been made to ensure accuracy with respect to numbers used (e.g. amounts, temperature, volume, time etc.) but some experimental errors and deviations should be accounted for.

EXAMPLES

Materials and Equipment

N-Hydroxysuccinimide (NHS)-activated magnetic agarose beads, ITO (Indium Tin Oxide) and gold-coated microscope slides, silicone gaskets, multi-well chambers and methods of preparing, assembling and measuring bead arrays are described in the U.S. patent application Ser. No. 16/125,164, publication No. US 2019-0072546 A1.

Unless noted otherwise, consumables such as microcentrifuge tubes, pipette tips, weigh boats etc, were standard research grade. Reagents such as organic solvents, acids, salts, buffers, detergents, MALDI matrices etc, were standard research grade with a purity of 99% or higher and used as received from the manufacturer without further purification. Standard lab equipment included a microcentrifuge, a microplate centrifuge, magnetic tube racks, microtiter plate shaker, vortexer, etc.

Proteases trypsin, chymotrypsin, LysC, LysN, AspN, ArgC and GluC were from either Promega (Madison Wis.) or New England Biolabs (Ipswich Mass.). All proteases were sequencing grade. Digestion reactions with individual proteases were set up using a buffer, temperature and enzyme-to-substrate ratio that were recommended by the manufacturer. The duration of digestion reactions was typically overnight (18 hrs).

Programmable robotic liquid sprayer iMatrixSpray that is capable of dispensing MALDI matrix solutions was from Tardo GmbH (Subingen, Switzerland).

Matrix Assisted Laser Desorption Ionization Time of Flight (MALDI TOF) MS data was acquired on Bruker Daltonics (Billerica MA) Autoflex Speed MALDI TOF-TOF mass spectrometer using FlexControl v.3.4 software and low mass range data acquisition methods supplied by the manufacturer. Unless otherwise indicated, mass spectra were acquired in the positive linear mode, 900-7000 m/z mass range using the laser repetition rate of 2 kHz. Between 2000 and 10000 single shot spectra were collected from individual microarray spots using the random walk method. The instrument laser power was 50%, laser attenuator offset 30%, attenuator range 20%. The voltage settings were 19.50 kV (ion source 1), 18.35 kV (ion source 2) and 6.0 kV (lens). The pulsed ion extraction was 130 ns. The detector gain voltage was 4.0× or 2910 V.

In the positive reflector mode, the spectra were measured in the 900-5000 m/z mass range using the laser repetition rate of 2 kHz. The voltage settings were 19.00 kV (ion source 1), 16.55 kV (ion source 2), 8.45 kV (lens), 21.00 kV (reflector), 9.65 kV (reflector 2). The pulsed ion extraction was 100 ns. The detector gain voltage was 8.1× or 1919 V. The digitizer sampling rate was 4.00 GS/s.

In the MS-MS mode, the spectra were collected using the LIFT method provided by the manufacturer at the laser repetition rate of 2 kHz (parent ions) and 200 Hz (fragment ions). The voltage settings were 6.00 kV (ion source 1), 5.30 kV (ion source 2), 3.00 kV (lens), 27.20 kV (reflector), 11.70 kV (reflector 2), 19.00 kV (lift 1), 4.20 kV (lift 2). The pulsed ion extraction was 100 ns. The reflector gain voltage was 19.4× or 2051 V. The digitizer sampling rate was 2.00 GS/s.

The Autoflex Speed instrument was externally calibrated in cubic enhanced mode using a mixture of peptides derived from trypsin-digested CAM-modified bovine serum albumin (BSA) supplemented with human insulin and ubiquitin. Molecular weights of the calibration peptides spanned a range between 800 and 8000 Da.

Prior to MS data acquisition, analyte-containing spots within each microarray were identified by visual inspection and their coordinates submitted to AutoXecute module of FlexControl. The analyte-containing spots were identified based on their characteristic appearance due to presence of inner areas devoid of the MALDI matrix that coincide with previous locations of beads on the microarray slide. MS data was subsequently acquired from the selected spots in auto-matic mode. Mass spectra collected from each spot were averaged and the averaged spectra from each spot were individually saved.

Mass spectra were processed and analyzed using FlexAnalysis v.3.4 software. Peaks were detected that had a signal-to-noise ratio of at least 3. In some cases, baseline subtraction procedure was applied to individual mass spectra.

Unless otherwise indicated, peaks in the mass spectra are labeled using average and not monoisotopic m/z values. The peptide masses are also provided as average and not monoisotopic values unless indicated otherwise.

Peptide sequencing data was produced using the LIFT method and analyzed using program MS-Tag (ProteinProspector, University of California San Francisco). Typical MS-Tag settings were: database: SwissProt 2017.11.01; taxonomy: Homo Sapiens; digest: no enzyme; constant mods: carbamidomethyl (C); variable mods: acetyl (K), deamidated (R), methyl (K), dimethyl (K), dimethyl (uncleaved R), trimethyl (uncleaved K), phospho (ST), Gln->pyro-Glu (N-term Q), oxidation (M); parent ion tolerance: 200 ppm; fragment tolerance: 300 ppm; max mods: 4; instrument: MALDI-TOFTOF.

In some cases, peaks were assigned to specific peptides based on their predicted molecular weights.

HeLa cells were cultured in RPMI media with 10% fetal bovine serum (FBS), 1× Pen-Strep (Sigma-Aldrich, St. Louis MO, #P4333) to 75% confluence at 37° C. with 5% $CO_2$. Cells were washed twice with cold PBS. PBS was removed, and cells were scraped in urea lysis buffer (9 M sequence grade urea, 20 mM HEPES pH 8.0, 1 mM β-glycerophosphate, 1 mM sodium vanadate, 2.5 mM sodium pyrophosphate). Cells were sonicated 3 times for 20 s each at 15 W output power with 1 minute cooling on ice between each burst. Sonicated lysates were centrifuged for 15 min at 10° C. at 20,000×g.

Protein lysates were collected and reduced with 4.5 mM DTT for 30 min at 40° C. Reduced lysates were alkylated with 10 mM iodoacetamide for 15 min at room temperature in the dark. Samples were diluted 1:4 with 0.2% ammonium bicarbonate (pH 8.0) and digested overnight with 10 µg/mL trypsin-TPCK (Promega) in 1 mM HCl or another protease. Digested peptide lysates were desalted over 360 mg SEP PAK Classic C18 columns (Waters, Milford MA, #WAT051910). Peptides were eluted with 40% acetonitrile in 0.1% TFA, dried under vacuum in a lyophilizer and stored at -80° C.

Protein concentration measurements were performed using Bradford protein assay (Life Technologies, Carlsbad CA, #23236) following the manufacturer's protocol.

Human post-mortem brain tissue samples were obtained from the dorsolateral prefrontal cortex (Brodmann area 9). 3 control samples were from individuals with no history of neurological disorders. 3 diseased samples were from individuals diagnosed with Alzheimer's disease. The weight of individual tissue samples ranged from 4.8 to 6.4 mg.

Pooled normal and diseased brain samples were prepared by combining 0.5 mg tissue material from each of the 3 respective samples.

Each tissue sample was individually cooled in liquid nitrogen for 15 minutes and pulverized using a Bessman tissue pulverizer. The pulverized material was transferred to a 50 mL polypropylene conical tube. Urea lysis buffer was added to bring the total protein concentration to 2 mg/mL. The sample was combined with 200 µL of zirconium beads (BioSpec Products, Bartlesville OK, #11079101z), transferred to a 2 mL screw cap tube and homogenized using a bead beater (Biospec Products, #2025856).

The homogenized tissue samples were sonicated as previously described, the lysates were cleared by centrifugation for 15 min at 10° C. at 20,000×g and transferred into new tubes.

Protease digestion was performed according to the manufacturer's protocols. For example, samples for LysC digestion were diluted 1:6 in 50 mM Tris-HCl (pH 8.0), 1 mM EDTA to bring urea concentration below 2M. LysC protease (Promega #VA1170) was added to a final 1:50 enzyme to substrate ratio. The solutions were incubated overnight at 37° C. with shaking.

Samples were acidified with 20% TFA for a final TFA concentration of 1% and incubated on ice for 15 min. The acidified solutions were centrifuged for 15 min at 1,780 rcf (g). The peptide-containing supernatant was transferred into a new tube without dislodging the precipitate. Samples were purified using C18 BioPureSPN MACRO spin columns (Nest Group, Southborough Ma, #HMM S18R) following the manufacturer's protocol. The eluate was frozen at −80° C. for 24 hours and lyophilized for 48 hours Unless noted otherwise, histone enrichment methods such as isolation of nuclei or isolation of nucleosomes were not utilized during the processing of biological materials.

EXPERIMENTAL RESULTS

Some of the experiments performed using the disclosed assays and methods and the resulting experimental data are described below.

Example 1

Multiplexed Bead Array for Measuring Distinct PTM Sites within Human Histone H3

ABFLEX® recombinant antibodies (rAbs) were purchased from Active Motif (Carlsbad, Calif.). All antibodies were supplied as purified IgG at a concentration of 1 mg/mL in 200 mM Hepes pH 7.5, 100 mm NaCl, 50 mM NaOAc, 30% glycerol and 0.035% sodium azide. Individual antibodies included histone H3K9ac antibody (catalog number 91104), histone H3K9me0 antibody (catalog number 91156), histone H3S10ph antibody (catalog number 91132), histone H3K27ac antibody (catalog number 91194), histone H3K27me3 antibody (catalog number 91168).

Each antibody was individually conjugated to NETS-activated magnetic agarose beads using the previously described procedures. Individual magnetic beads had a diameter between 0.35 and 0.38 mm and contained approximately 0.07 μg of an antibody.

5-plex bead arrays were assembled by combining beads conjugated to one of the 5 histone-specific antibodies. A total of 3 replicate beads were included in a bead array. Therefore, each bead array contained a total of 15 beads. A total of 96 bead arrays were produced and stored in individual wells of a 96 multi-well plate at 4° C. for up to 6 months. The bead arrays were stored in 1×PBS buffer supplemented with 0.03% sodium azide.

Example 2

Validation of Antibodies for Capturing Proteolytic Fragments of Histone H3

Test samples were prepared from cultured HeLa cells that were subjected to lysis, disulfide bond reduction, cysteine alkylation, proteolytic digestion, C18 desalting and lyophilization using the previously described methods. Individual samples were prepared by digestion with one of the following proteases: trypsin, chymotrypsin, LysC, ArgC, AspN and GluC. Approximately 300 μg of total input protein was used for each enrichment reaction.

Each of the 5 antibodies described in the previous Example was individually validated to confirm their ability to specifically bind one or multiple fragments of histone H3 from enzymatically digested HeLa lysates. The validation procedure included steps of incubating reactive sites containing a particular antibody with a test sample, washing the reactive sites to remove non-specifically bound compounds, analyzing the reactive sites by MS and identifying specifically captured fragments of histone H3 in the mass spectra.

Antibodies #91104, #91194 and #91168 were confirmed to specifically recognize fragments of histone H3 containing the respective PTM sites.

Furthermore, it was experimentally established that while the #91104 antibody specifically recognized acetylated Lys9 within a sequence of histone H3, its specificity was limited to fragments of histone H3 that did not contain PTM sites adjacent to Lys9. In other words, the #91104 antibody did not appear to recognize acetylated Lys9 that was adjacent to citrullinated Arg8 and/or phosphorylated Ser10.

Example 3

Microarray Reactive Sites that Recognize Adjacent Fragments of a Histone

The microarray reactive sites containing antibodies #91104 (H3K9ac) and #91194 (H3K27ac) are able to recognize adjacent fragments of a protein, in this case histone H3. The Lys9 and Lys27 sites are located sufficiently close yet the sequence between the two sites (K)STGGKAPRKQLATKAAR(K) (disclosed as SEQ ID NO: 1 (with terminal residues) and SEQ ID NO: 2 (without terminal residues)) contains cleavage sites that are recognized by several proteolytic enzymes, including chymotrypsin, pepsin and ArgC. For example, chymotrypsin recognizes a single site (Leu20), while ArgC potentially recognizes two sites (Arg17 and Arg26). However, ArgC may not cleave a site adjacent to a PTM site, e.g. it would skip over Arg26 if Arg26 is adjacent to an acetylated or methylated Lys27. The histone H3 sequence between the N-terminus and Lys9 contains no proteolytic cleavage sites recognized by chymotrypsin. The first proteolytic cleavage site recognized by chymotrypsin after Leu20 is Tyr41. Therefore, incubating the described 2-plex bead array with a sample that contains fragments of chymotrypsin-digested histone H3 enables analysis of a contiguous stretch of more than 30 amino acids from the N-terminus to well beyond Lys27 in just 2 fragments with no gaps in the sequence coverage. Using additional antibodies that recognize sites beyond Lys27 will enable probing of a larger portion of a sequence, up to the entire sequence of histone H3 with no gaps in the sequence coverage.

The described method may be used to probe other histones and proteins other than histones. One of the benefits of measuring a contiguous stretch of a protein sequence in multiple fragments with no gaps between individual fragments is the ability to obtain complete sequence information including locations of single-site mutations and PTM sites.

Example 4

Microarray Reactive Sites that Recognize Distinct Sequence Variants of a Histone The bead array described in the previous Example contains distinct reactive sites that are capable of capturing fragments of histone H3 that contain amino acids Ala1-Leu20 and Ala21-Tyr41 from chymotrypsin-digested samples. The former fragments are captured by the H3K9ac antibody and the latter fragments are captured by the H3K27ac antibody if they contain the recognized PTM sites: acetylated Lys9 and acetylated Lys27, respectively. The Ala1-Leu20 sequence is identical in histone sequence variants H3.1, H3.2 and H3.3. The Ala21-Tyr41 sequence is not identical as histones H3.1 and H3.2 contain alanine in position 31 while histone H3.3 contains serine.

Therefore, the described bead array contains a reactive site (H3K9ac) that recognizes fragments that are identical across multiple sequence variants of a histone and a separate reactive site (H3K27ac) that recognizes fragments that are not identical in distinct sequence variants of the histone, i.e. have different sequence and molecular weight.

Example 5

Microarray Reactive Sites that Recognize an Isolated PTM Site and Adjacent PTM Sites Acetyl- and phospho-histone H3 (Lys9/Ser10) antibody is available from Cell Signaling Technology (Danvers MA), catalog #9711. The #9711 antibody recognizes only fragments of histone H3 that contain acetylated lysine 9 and phosphorylated serine 10.

By contrast, the #91104 antibody recognizes only fragments of histone H3 that contain acetylated lysine 9 and non-phosphorylated serine 10. A bead array that includes a reactive site containing antibody #9711 and a separate reactive site containing antibody #91104 is capable of separately capturing fragments of histone H3 that contain acetylated Lys9 in the presence and in the absence of phosphorylated Ser10, respectively. Further including a reactive site containing antibody #91156 (H3K9me0) enables capturing fragments of histone H3 that contain non-acetylated and non-methylated Lys9.

Example 6

Epigenetic Analysis of Histone Modifications in Normal and Diseased Samples

A group containing 3 normal brain samples and 3 diseased brain samples was prepared using digestion with LysC endoprotease. The samples were individually analyzed using 3-plex assays containing antibodies specific for H3K9ac, H3K27ac and H3K27me3.

Figure 3:
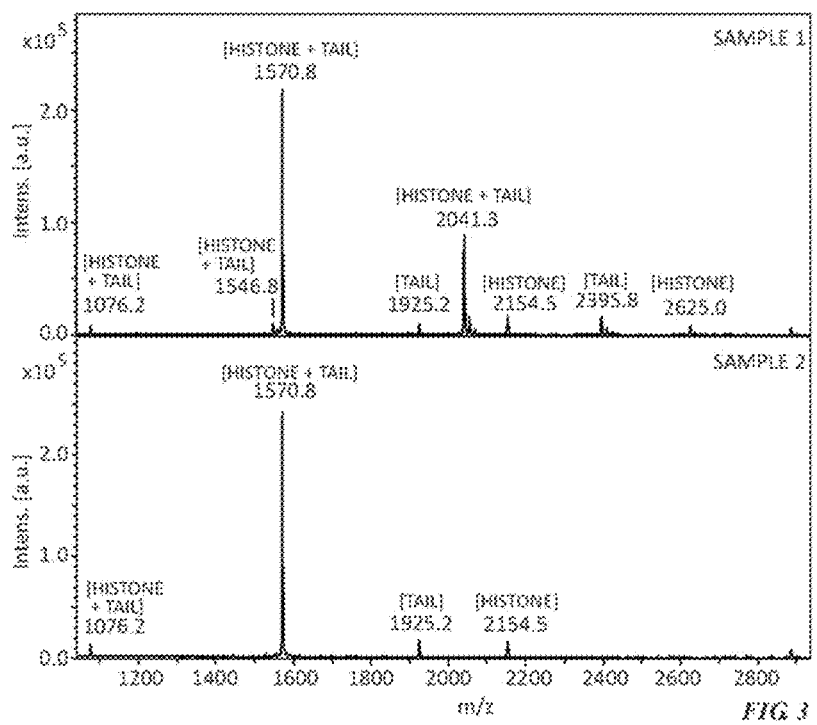
FIG. 3 shows linear MALDI TOF mass spectra of brain samples obtained using LysC digestion and H3K9ac enrichment in the 1050-2900 m/z mass region.

FIG. 3 shows exemplary mass spectra obtained from 2 of the 6 samples using the H3K9ac enrichment. Several peaks were detected and assigned to proteolytic fragments of histone H3. Strong to medium intensity peaks at 1076.2, 1570.8, 1925.2 and 2154.5 m/z are detected in all samples. The 1076 peak is assigned to a fragment Gln5-Lys14 of histone H3 that contains 1 missed cleavage site and 1 acetylated lysine (Lys9). The 1570 peak is assigned to a fragment Gln5-Lys18 that contains 2 missed cleavage sites and 2 acetylated lysines (Lys9 and Lys14). The 2154 peak is assigned to a fragment Gln5-Lys23 that contains 3 missed cleavage sites and 3 acetylated lysines (Lys9, Lys14 and Lys18). The 1925 peak is assigned to a fragment Gln5-Ala21 that contains 3 missed cleavage sites, 3 acetylated lysines (Lys9, Lys14 and Lys18) and terminates at a known site of histone tail clipping. The 1076, 1570, 1925 and 2154 peaks appear without nearby peaks located within 14, 28 or 42 m/z indicating absence of peptides containing mono-, di- or tri-methylated residues in the Lys9ac-enriched fraction of histone H3 fragments containing residues 5 through 23.

By contrast, strong to medium intensity peaks at 1546.8, 2041.4, 2395.8 and 2625.0 m/z are detected in 2 normal samples and 1 diseased sample but have dramatically (greater than 10-fold) reduced intensity in 1 normal and 2 diseased samples. The 1546 peak is assigned to a fragment Ala1-Lys14 that contains 2 missed cleavage sites (Lys4 and Lys9), 1 acetylated lysine (Lys9) and 1 mono-methylated lysine (Lys4). The 2041 peak is assigned to a fragment Ala1-Lys18 that contains 3 missed cleavage sites, 2 acetylated lysines (Lys9 and Lys14) and 1 mono-methylated lysine (Lys4). The 2395 peak is assigned to a fragment Ala1-Ala21 that contains 4 missed cleavage sites, 3 acetylated lysines (Lys9, Lys14 and Lys18), 1 mono-methylated lysine (Lys4) and terminates at the histone tail clipping site Ala21. The 2625 peak is assigned to a fragment Ala1-Lys23 that contains 4 missed cleavage sites, 3 acetylated lysines (Lys9, Lys14 and Lys18) and 1 mono-methylated lysine (Lys4). The 1546, 2041, 2395 and 2625 peaks all appear with nearby peaks that are shifted by +14 and +28 m/z indicating presence of peptides containing di- and tri-methylated residues (Lys4) in the Lys9ac-enriched fraction of histone H3 fragments containing residues 1 through 23. It is noted that acetylation and tri-methylation produce similar mass shifts of about 42 m/z that may not be easily distinguished by linear TOF MS although they are distinguishable using reflector TOF MS and other types of MS.

Lower intensity peaks were also detected at 2496.9, 2510.9 and 2524.9 m/z in the spectra containing the 2395 peak. The 2496 peak is assigned to a fragment Ala1-Thr22 that contains 4 missed cleavage sites, 3 acetylated lysines (Lys9, Lys14 and Lys18), 1 mono-methylated lysine (Lys4) and terminates at the histone tail clipping site Thr22. The 2510 and 2524 peaks are assigned to Ala1-Thr22 fragments containing acetylated Lys9, Lys14, Lys18 and di- and tri-methylated Lys4 respectively. The described method enables using a PTM-specific capture agent to detect in a same mass spectrum at least 3 histone fragments that are cleaved at 2 adjacent sites (terminal amino acid residues) by one or more than one endogenous protease. In the described Example, at least 6 histone fragments terminating at 2 adjacent terminal sites (Ala21 and Thr22) are detected, each fragment containing 3 acetylated sites (Lys9, Lys14 and Lys18) and a mono-, di- or trimethylated site (Lys4).

The described method uses site-specific digestion of a histone with an enzyme (LysC) that generates a missed cleavage if it encounters a PTM site, in this case lysine that is acetylated or mono-, di- or tri-methylated. Histone fragments containing at least 1, as many as 4, and more than 4 missed cleavage sites are detectable in the 800-7,000 m/z mass range using affinity capture on a single bead. Multiple missed cleavages produce a mass spectrum containing peaks from peptides with distinct combinations of PTM sites. Such distinct peptides are detected simultaneously in a mass spectrum enabling rapid screening of co-localized PTM sites. The cleaved histone tails are detected at distinct m/z values compared to fragments of intact histone H3 containing same PTM sites, as evidenced by the peaks at 1925 and 2154 m/z, respectively. This allows independent analysis of PTM sites in full-length histones and clipped histone tails. For example, it was observed that similarly to intact histones, the clipped histone tails contain significant amounts of acetylated Lys9, Lys14 and Lys18 and also significant amounts of co-occurring mono-, di- and tri-methylated Lys4, as evidenced by the peaks at 2395 and 2625 m/z, respectively. Other signals in the mass spectrum contain contributions from both the intact histones and the clipped histone tails. For example, the 1076 and 1570 m/z peaks likely contain contributions from peptides that are produced by LysC digestion of both intact histones and clipped histone tails at sites Lys4/Lys14 and Lys4/Lys18, respectively.

The mass spectrum shown in FIG. 3 contains: (1) a signal from a peptide that is derived from a clipped tail of a histone (the 2395 m/z peak, fragment Ala1-Ala21), (2) a signal from a peptide derived in part from a clipped tail of a histone and in part from a non-clipped histone (the 2041 m/z peak, fragment Ala1-Lys18), and (3) a signal from a peptide derived from a non-clipped histone (2625 m/z peak, fragment Ala1-Lys23).

As described below, the instant specification also contains evidence for histone tail clipping occurring in some cases past residue Thr32 in histone H3. Thus, it is possible that the detected 2154 and 2625 peaks that are currently assigned to intact histone H3 fragments that terminate at Lys23 may in fact contain at least some contributions from the longer cleaved histone tails. This may be verified by including a reactive site in a bead array that contains an antibody that specifically recognizes a histone H3 site located closer to the C-terminus. For example, an antibody may recognize a sequence surrounding Lys79 in histone H3. An example of such antibody is Di-Methyl-Histone H3 (Lys79) antibody, catalog #5427 from Cell Signaling Technology.

This Example demonstrates the ability to detect in a same mass spectrum histone fragments obtained from intact histones and from cleaved histone tails and distinguish them based on their distinct molecular weights. It also demonstrates the ability to detect signals from co-occurring modifications at Lys4 (methylation) and Lys9 (acetylation) and to use the detected signals to profile groups of samples obtained from subjects that either have or are suspected of having a neurological disease and from normal (control) subjects. A spectral signature consisting of peaks at 1546, 2041, 2395 and 2625 m/z was observed that may be used to distinguish human brain tissue samples obtained from different subjects.

The high specificity of LysC digestion ensures that any non-specifically cleaved histone fragments may be confidently identified as products of endogenous proteolytic activity that occurs in the sample, e.g. cleavage by cathepsin L.

Example 7

MS Analysis of Clipped Histone Tails

The normal and diseased pooled brain samples were digested with AspN protease. The sequence of histone H3.1 contains few AspN recognition sites, Gln76-Asp77 being the closest to the N-terminus. Digesting histone H3.1 or other histone H3 sequence variants with AspN is expected to generate N-terminal fragments having molecular weights greater than 8,500 Da. Even if histone tail clipping occurs, for example at the Ala21-Thr22 site, the size of N-terminal fragments of a clipped histone generated by AspN-specific digestion would still be greater than 6,000 Da.

Yet, mass spectra of AspN-digested normal and diseased brain samples obtained using bead arrays containing the H3K9ac, H3K27ac and H3K27me3 reactive sites revealed multiple peaks below 5,200 m/z with particularly strong peaks appearing below 3,000 m/z. Based on the specificity of AspN digestion and immunoaffinity enrichment, the detected signals are therefore assigned to cleaved tails of histone H3 generated by endogenous proteolytic activity.

Figure 4A:
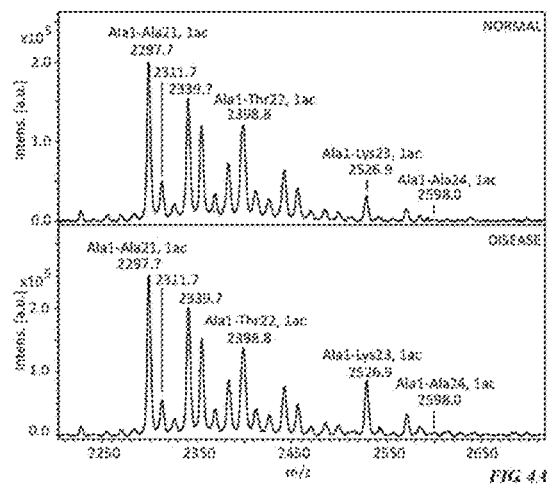
FIG. 4A shows linear MALDI TOF mass spectra of normal and diseased brain samples obtained using AspN digestion and H3K9ac enrichment in the 2250-2650 m/z mass region.

FIG. 4A shows mass spectra of the normal and diseased brain samples recorded from a single H3K9ac reactive site in the 2250-2750 m/z spectral range. Multiple peaks are detected in that mass range with individual peaks spaced apart by about 14 m/z. Several peaks are assigned to peptides containing the first 21 N-terminal amino acids of histone H3, beginning at Ala1 and terminating at Ala21. All peptides contain one or more than one PTM sites. Because of the specificity of H3K9ac antibody enrichment, all peptides contain acetylated Lys9, while many peptides contain additional modifications such as acetylation and/or mono-, di- or tri-methylation at Lys4, Lys14 and Lys18. A strong peak at 2297.7 m/z is assigned to fragment Ala1-Ala21 containing a single acetylated site, Lys9. Peptides containing up to 4 acetylated sites are detectable in the mass spectrum (see also FIG. 4B).

Peaks at higher m/z values are assigned to longer fragments of histone H3 that contain residues beyond Ala21. For example, a peak at 2398.8 m/z is assigned to fragment Ala1-Thr22 containing a single acetylated site (Lys9), while a peak at 2526.9 m/z is assigned to fragment Ala1-Lys23 also containing acetylated Lys9. The 2398 and 2526 peaks are accompanied by peaks shifted by +14, +28 and +42 m/z confirming the presence of multiple PTM sites in these longer fragments. The overall pattern of PTM sites observed for the Ala1-Ala21 fragment is similar to the pattern observed for the Ala1-Thr22 fragment.

The assay described in this Example includes the steps of digesting a protein using a protease that generates sufficiently large fragments of the protein, e.g. larger than 6 kDa, larger than 8 kDa or larger than 10 kDa and then specifically capturing and subsequently detecting by MS fragments of the protein that are smaller than the fragments produced by the protease digestion, e.g. smaller than 6 kDa, smaller than 8 kDa or smaller than 10 kDa.

Example 8

Estimation of Relative Abundances of Multiple Fragments of a Histone

The spectral data shown in FIG. 4A was used to obtain an estimate of relative abundances of various fragments of histone H3, both within a same sample (upper trace) and between different samples (upper and lower traces) using relative intensities of the corresponding peaks in the mass spectra and without using spiked-in internal standards. This approach is feasible because individual peptides in the enriched histone fractions have similar length and amino acid composition and therefore similar ionization efficiency in the MALDI TOF process. It was verified that mass spectra containing signals from multiple (more than 10) fragments of a histone are highly reproducible when measured from distinct replicate reactive sites of a bead array, with a coefficient of variation (CV) being less than 10% and often less than 5%.

In an example of measuring relative abundances within a single sample, fragments Ala1-Ala21 containing 1 and 2 acetylated lysines (peaks at 2297.7 and 2339.7 m/z, respectively) were estimated to have similar abundance, while fragment Ala1-Ala21 containing 1 acetylated lysine (peak at 2297.7 m/z) was estimated to be more abundant than fragment Ala1-Ala21 containing 1 acetylated lysine and 1 monomethylated lysine (peak at 2311.7 m/z).

In an example of measuring relative abundances in two or more samples, the upper and lower traces in FIG. 4A were normalized such that the 2297 peaks had equal intensities in both spectra. It was observed that relative intensities of the 2398 peaks were also similar in the two spectra indicating similar abundance of the Ala1-Ala21 fragment relative to the Ala1-Thr22 fragment in the normal and diseased samples. The 2526 peak was more intense in the diseased sample indicating greater abundance of the Ala1-Lys23 fragment relative to the Ala1-Ala21 fragment in the diseased sample compared to the normal sample.

All peaks detected in the mass spectra shown in FIG. 4A are assigned to cleaved tails of histone H3 that are produced by endogenous proteolytic activity that occurs in the sample, in this case normal and diseased human brain.

Example 9

Measurement of Histone Fragments in the MALDI TOF Reflector Mode

Figure 4B:
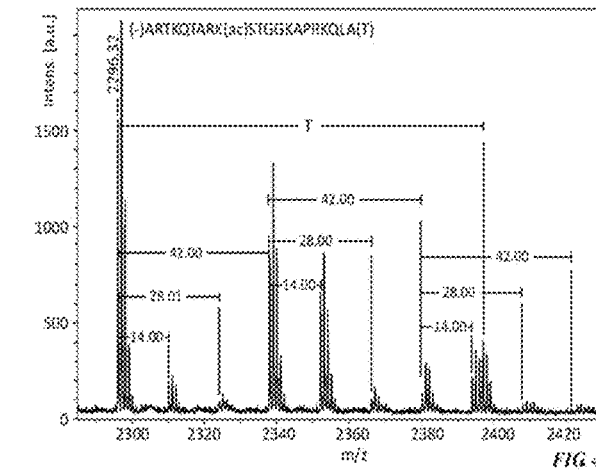
FIG. 4B shows reflector MALDI TOF mass spectrum of a diseased brain sample obtained using AspN digestion and H3K9ac enrichment.

FIG. 4B shows a mass spectrum of the H3K9ac enrichment obtained from the AspN digested diseased brain sample and recorded in the MALDI TOF reflector mode. The monoisotopic resolution of the reflector mass spectrum confirms the previously made peak assignments from the MALDI TOF linear spectra. For example, the observed pattern of peaks shifted by 42.01 from the 2296.33 m/z peak (monoisotopic) confirms the presence of multiple Ala1-Ala21 fragments containing up to 4 acetylated sites (Lys4, Lys9, Lys14, Lys18).

The cluster of peaks near 2400 m/z is resolved into two distinct groups: a peak at 2394.37 m/z (monoisotopic) is assigned to fragment Ala1-Ala21 containing 3 acetyl and 1 methyl groups while the peak at 2397.38 is assigned to fragment Ala1-Thr22 containing 1 acetyl group (Lys9).

Example 10

Peptide Ladder at the N-Terminus of Histone H3 and Clipped Histone Tails

Figure 5:
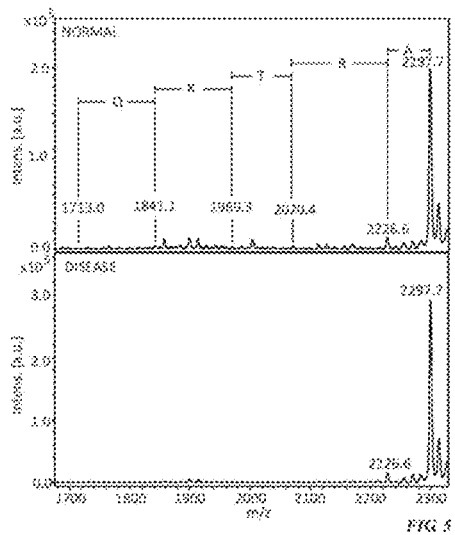
FIG. 5 shows mass spectra of normal and diseased brain samples obtained using AspN digestion and H3K9ac enrichment in the 1700-2300 m/z mass region.

FIG. 5 shows mass spectra of the H3K9ac enriched fraction of the AspN-digested normal and diseased brain samples in the 1700-2300 m/z region. The pattern of peaks reveals a peptide ladder, that is a group of histone fragments that start at adjacent residues located at the N-terminus of histone H3. The peak at 2297.7 m/z was previously assigned to the fragment Ala1-Ala21 containing acetylated Lys9. A peak at 2226.6 m/z that is shifted by −71 m/z from the 2297 peak is assigned to a fragment of histone H3 containing residues Arg2-Ala2: (A)RTKQTARK(ac)STGGKAPRKQLA(T) (disclosed as SEQ ID NO: 3 (with terminal residues) and SEQ ID NO: 4 (without terminal residues)) that has a single terminal amino acid (Ala1) missing. That peptide contains acetylated Lys9 and terminates at the histone tail clipping site Ala21. The 2226 peak is accompanied by lower intensity peaks shifted by +14, 28, 42 and 56 m/z due to methylations and/or acetylations on residues other than Lys9.

Additional peaks are detected at 2070 m/z (−156 m/z shift from the 2226 peak, removal of Arg2), 1969 m/z (−101 m/z shift from 2070 peak, removal of Thr3) and 1841 m/z (−128 m/z shift from 1969 peak, removal of Lys4). Weaker peaks are detected below 1841 m/z indicating presence of even smaller peptides, such as Thr6-Ala21. The 1841, 1969 and 2070 peaks are accompanied by peaks that are shifted by +14, 28, 42 and 56 m/z from the parent peaks due to methylation(s) and/or acetylation(s).

This Example demonstrates detection of an N-terminal peptide ladder Ala1-Arg2-Thr3-Lys4-Gln5 (SEQ ID NO: 5) that possibly extends beyond Gln5 in histone H3. The peptide ladder is detected in a sample that contains cleaved tails of histone H3, however the described method may be also applied to detect sequentially cleaved N-terminal residues that occur in full-length histones H3, as well as histones other than H3.

Note that common digestive enzymes trypsin, ArgC and LysC may interfere with detection of the N-terminal peptide ladder in histone H3 as these enzymes cleave after Arg2 and/or Lys4.

A study by Liu et al (Clipping of arginine-methylated histone tails by JMJD5 and JMJD7, PNAS Sep. 12, 2017, 114 (37), E7717-E7726) has previously reported endo- and exoproteolytic activities of enzymes JMJD5 and JMJD7 that cause cleavage of a dipeptide Ala1-Arg2me2 followed by sequential removal of adjacent residues Thr3, Lys4, Gln5, Thr6 and Ala7 from a synthetic peptide substrate.

The assay disclosed in the instant specification is substantially different from the work of Liu et al in several aspects. First, it detects an exonuclease activity that results in a removal of the N-terminal Ala1, while the Liu assay detects an endoprotease activity that results in a removal of a dipeptide Ala1-Arg2me. Second, the current assay detects removal of Arg2 that is not modified while the Liu assay requires a di-methylated arginine. Third, the current assay detects the proteolytic activity that occurs in vivo, in tissues and/or cells while the Liu assay is an in-vitro assay that utilizes a synthetic peptide and a specific enzyme. Furthermore, the current assay may be combined with an assay that detects the C-terminal peptide ladder in cleaved histone tails thereby enabling studies of histone clipping events that are facilitated by more than one protease.

Example 11

Diagnostic Utility of the N-Terminal Peptide Ladder of Histone H3

The previously described histone N-terminal peptide ladder assay and the relative abundance assay were used to compare the normal and diseased human brain samples after the AspN digestion and H3K9ac enrichment. The top and bottom traces in the mass spectra shown in FIG. 5 were normalized using intensity of the 2297 peak from the monoacetylated Ala1-Ala21 fragment of histone H3. It was observed that peaks between 2,226 and 2,297 m/z, which are assigned to acetylated and/or methylated fragments Arg2-Ala21 of histone H3, also have similar intensity between the normal and diseased samples. By contrast, the majority of peaks below 2,226 m/z, which are assigned to fragments missing residues Arg2 through Lys4, have 3- to 10-fold lower intensity in the diseased sample. The low intensity of peaks in the diseased sample is particularly noticeable in the spectral region that contains signals from the peptides that start at Lys4.

It was concluded that relative to the normal sample, the diseased sample has lower abundance of histone H3 fragments that start at Thr3 or Lys4, terminate at Ala21 and contain acetylated Lys9. The diseased and normal samples have similar abundance of fragments that start at Ala1 or Arg2, terminate at Ala21 and contain acetylated Lys9

This Example demonstrates a diagnostic utility of an assay that involves detection and quantification of multiple fragments of a histone that start at adjacent residues at the N-terminus of the histone. The assay includes affinity capturing multiple peptides that have been clipped from a histone, using MS to measure intensities of signals from individual peptides in the captured fraction, using the acquired MS data to detect changes in relative abundances of individual peptides in the captured fraction and correlating the detected changes in relative abundances with a disease status of the sample and/or with a status of a biological or a disease pathway that is altered in the sample.

More broadly, this Example demonstrates an analytical utility of an assay that uses antibody-based detection of multiple cleaved tails of a histone. In some cases, the multiple cleaved tails contain a peptide ladder at the N-terminus and/or at the C-terminus Example 12

Peptide Ladder at the C-Terminus of Histone H3 and Clipped Histone Tails

Figure 6:
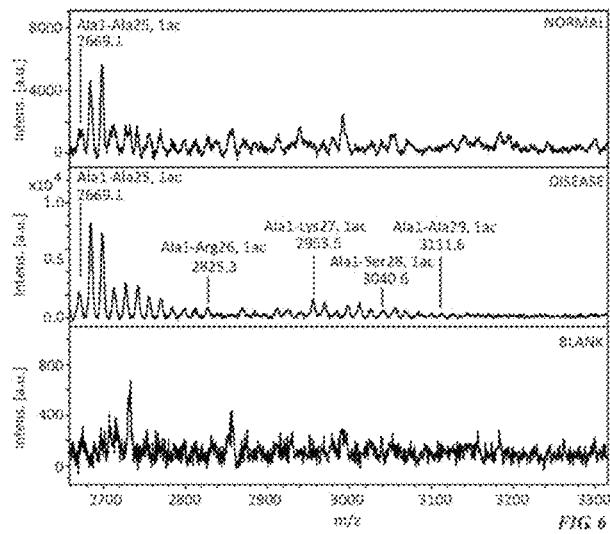
FIG. 6 shows mass spectra of normal and diseased brain samples obtained using AspN digestion and H3K9ac enrichment and a negative control in the 2700-3300 m/z mass region.

FIG. 6 shows mass spectra of the H3K9ac enriched fraction of the AspN-digested normal and diseased samples in the 2700-3300 m/z region. A blank spectrum obtained from the AspN-digested diseased sample using an antibody other than H3K9ac is also shown. A peak is detected at 2669.1 m/z and assigned to an acetylated fragment of histone H3 containing residues Ala1-Ala25: (−)ARTKQTARK(ac)STGGKAPRKQLA(T) (disclosed as SEQ ID NO: 6 (with terminal residue) and SEQ ID NO: 7 (without terminal residue)). The 2669 peak is accompanied by lower intensity peaks shifted by +14, +28 and +42 m/z due to additional methylation and/or acetylation. Peaks were also detected in the diseased sample at 2825.3 m/z (fragment Ala1-Arg26), 2953.5 m/z (fragment Ala1-Lys27), 3040.6 m/z (fragment Ala1-Ser28) and 3111.6 m/z (fragment Ala1-Ala29), all fragments containing acetylated Lys9.

The combined data from FIG. 4A and FIG. 6 demonstrate a peptide ladder Ala21-Thr22-Lys23-Ala24-Ala25-Arg26-Lys27-Ser28-Ala29 (SEQ ID NO: 41) that is detected in a pool of cleaved tails of histone H3 obtained from a brain tissue. The peptide ladder contains more than 4 consecutively cleaved residues of histone H3.

The combined data in FIG. 4A, FIG. 5 and FIG. 6 demonstrate detection of histone tails that are sequentially cleaved on the N-terminal and C-terminal ends.

To rule out a possibility that the observed peptide ladders were a result of exo- and/or endoprotease activity that occurred during the sample preparation, proteolytic fragments of at least 20 distinct proteins other than histone H3 and also at least 20 distinct proteolytic fragments of a protein other than histone H3 were analyzed in the normal and diseased brain samples by bead-based affinity enrichment coupled with MS detection. N- and C-terminal peptide ladders were not detected in any of the non-histone proteins.

All peaks shown in FIG. 4A, FIG. 5 and FIG. 6 are assigned to clipped histone tails, i.e. to N-terminal fragments of histone H3 that were removed from the histone by an endogenous proteolytic activity, e.g. by cathepsin L and/or other proteases. By contrast, none of the peaks could be assigned to either full-length histone H3 or a truncated form of histone H3, i.e. to the C-terminal portion of the histone that is produced after tail clipping. Therefore, an assay may be configured to exclusively detect clipped histone tails without significant contributions from intact histones or C-terminal fragments of clipped histones. Such assay may have various applications including: (i) studies of a biochemical turnover of clipped histone tails in cells and/or tissues and their accumulation in cells and/or tissues in relation to a disease or an altered biological pathway; (ii) studies of co-localization of PTM sites in the histone N-terminus; (iii) studies of a relationship between PTM sites and histone tail clipping; (iv) discovery of novel histone tail clipping sites.

Example 13

Diagnostic Utility of the C-Terminal Peptide Ladder of Histone H3

The C-terminal peptide ladder assay described in the previous Example was used to compare the normal and diseased human brain samples. FIG. 6 shows that the histone H3 fragments that start at Ala1, terminate at residues Ala25 through Ala29 and contain acetylated Lys9 are consistently less abundant in the normal sample compared to the diseased sample when normalized to the 2297 m/z signal from the Ala1-Ala21 fragment.

The observed correlation may therefore be used in a diagnostic test to analyze tissue samples obtained from subjects that are suspected of having a disease, for example a neurological disease.

Example 14

Histone H3 Tail Cleavage Beyond Thr32

Figure 7:
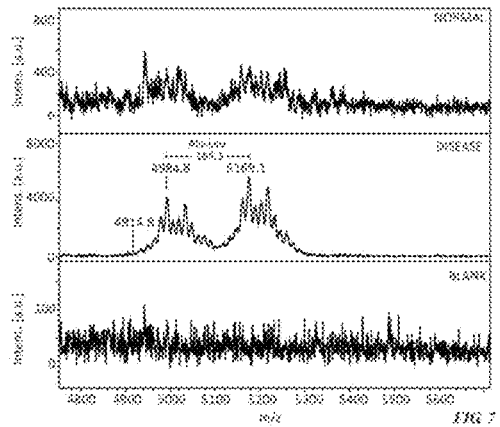
FIG. 7 shows mass spectra of normal and diseased brain samples obtained using AspN digestion and H3K9ac enrichment and a negative control in the 4800-5600 m/z mass region.

FIG. 7 shows mass spectra of the H3K9ac enriched fraction of the AspN-digested normal and diseased samples in the 4800-5600 m/z region. A blank spectrum obtained from the AspN-digested diseased sample using an antibody other than H3K9ac is also shown. Two broad spectral features containing multiple peaks separated by about 14 m/z are strong in the diseased sample, weak but still detectable in the normal sample and absent in the blank. These features are assigned to fragments of histone H3.1 and/or histone H3.2 that contain residues Ala1-Val46 (lower MW group) and Ala1-Leu48 (higher MW group). The lowest 1\4W peak in the Ala1-Val46 group is detected near 4914.8 m/z and assigned to a peptide containing a single acetylated lysine (Lys9). The highest MW peak in the Ala1-Val46 group is detected near 5110.9 m/z and assigned to a peptide containing 5 acetylated sites and either 2 mono-methylated sites or a di-methylated site. The Ala1-Val46 sequence contains 8 lysines that are known PTM sites including 5 lysines that are known acetylation sites. The strongest peak in this group is detected near 4984.8 m/z and assigned to a peptide containing 2 acetylated sites and either 2 mono-methylated sites or a di-methylated site The pattern of peaks in the Ala1-Leu48 group is nearly identical to the Ala1-Val46 group, consistent with the fact that both fragments contain the same number of lysines. The matching peaks in the two groups, e.g. 4984.8 and 5169.1 m/z peaks are separated by about 184.3 m/z, consistent with a mass of a dipeptide Ala-Leu. It is concluded that the mass spectra reveal two histone H3 cleavage sites: Val46 (Val46-Ala47 peptide bond) and Leu48 (Leu48-Arg49 peptide bond). The spectra do not show significant amount of the fragment Ala1-Ala47 indicating that cleavage at Ala47 either does not occur or occurs to a smaller extent compared to the two neighboring sites. The spectra shown in FIG. 7 may also contain contributions from the Ala1-Val46 and Ala1-Leu48 fragments of histone H3.3.

Example 15

Correlation Between PTM Status of Lys9 and Lys27 and the Tail Cleavage at Val46/Leu48

Figure 8:
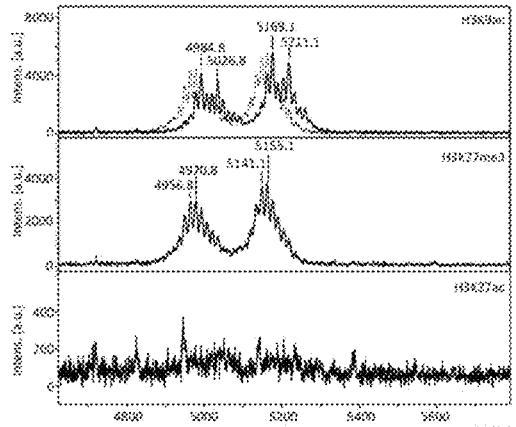
FIG. 8 shows mass spectra of diseased brain samples obtained using AspN digestion and H3K9ac, H3K27me3 and H3K27ac enrichments in the 4800-5600 m/z mass region.

FIG. 8 shows mass spectra of the H3K9ac-, H3K27me3- and H3K27ac-enriched fractions of the AspN-digested diseased sample in the 4800-5600 m/z region. The two broad spectral features previously observed in the H3K9ac enrichment are detectable in the H3K27me3 enrichment although the pattern of peaks is shifted by about 14 m/z toward the lower MW in the latter. One explanation is that the H3K27me3 antibody may specifically recognize H3K27me2 site. The most intense peaks are separated by 42 m/z in the H3K9ac enrichment and by 14 m/z in the H3K27me3 enrichment, corresponding to acetylation and mono-methylation mass shifts, respectively.

By contrast, no detectable signal was observed in this mass range for the H3K27ac enrichment indicating a strong correlation between the modification at Lys9 and Lys27 and the cleavage of histone tail that occurs at Val46 and Leu48.

Example 16

Diagnostic Utility of Histone H3 Fragments Terminating at Val46/Leu48

While the H3K9ac and H3K27me3 enrichments were able to capture a substantial amount of Ala1-Val46 and Ala1-Leu48 fragments from the diseased sample, they did not capture a detectable amount of these fragments from the normal sample. This result indicates that post-translationally modified fragments Ala1-Val46 and Ala1-Leu48 have diagnostic utility as markers of a neurological disease in a brain tissue and possibly in other human and animal tissues.

Example 17

Histone H3 Tails Cleaved at the N- and C-Termini

Figure 9A:
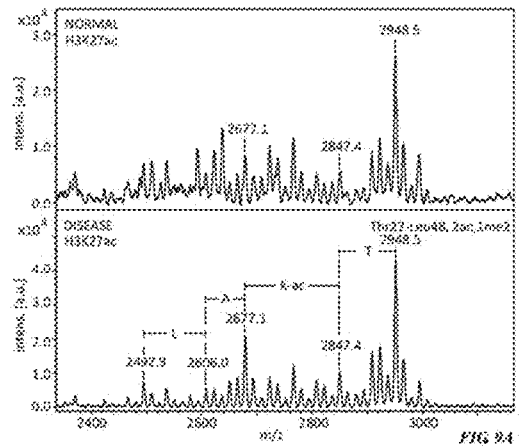
FIG. 9A shows mass spectra of normal and diseased brain samples obtained using AspN digestion and H3K27ac enrichment in the 2400-3000 m/z mass region.

FIG. 9A shows mass spectra of the H3K27me3 enriched fraction of the AspN-digested normal and diseased samples in the 2600-3100 m/z region.

Both spectra contain multiple strong peaks separated by 14, 28 and 42 m/z. The peak at 2692.2 m/z is assigned to the Thr22-Val46 fragment of histone H3.1 and/or histone H3.2 that contains 1 trimethyl and 1 methyl group at Lys27 and Lys36, respectively: (A)TKAARK(me3)SAPATGGVK(me)KPHRYRPGTV(A) (disclosed as SEQ ID NO: 8 (with terminal residues) and SEQ ID NO: 9 (without terminal residues)). The N- and C-termini of this peptide are histone tail clipping sites. The spectra also show existence of longer fragments, including Thr22-Ala47, Thr22-Leu48, Ala21-Leu48, Leu20-Leu48 and Ala21-Arg49 (weak), all fragments containing combinations of PTM sites that are similar to the PTM combinations in the Thr22-Val46 fragment.

The detection of Thr22-Val46 and Thr22-Leu48 fragments is in agreement with the previously demonstrated detection of Ala1-Val46 and Ala1-Leu48 fragments in the H3K9ac and H3K27me3 enrichments. Unlike the latter, the shorter fragments have similar abundance in the normal and diseased samples.

Figure 9B:
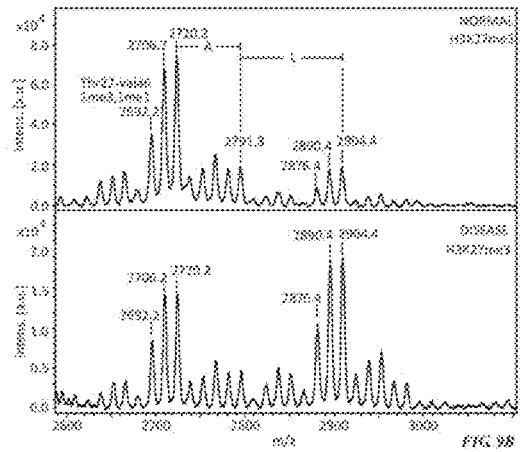
FIG. 9B shows mass spectra of normal and diseased brain tissue samples obtained using AspN digestion and H3K27me3 enrichment in the 2600-3000 m/z mass region.

FIG. 9B shows mass spectra of the H3K27ac enriched fraction of the AspN-digested normal and diseased samples in the 2400-3100 m/z region. While not identical, the normal and diseased samples have similar peak patterns including peak positions and relative intensities.

The strong peak at 2948.6 m/z is assigned to the Thr22-Leu48 fragment of histone H3.3 that contains 2 acetyl and 1 dimethyl group at Lys23, Lys27 and Lys36, respectively: (A)TK(ac)AARK(ac)SAPSTGGVK(me2)KPHRYRPGTVAL(R) (disclosed as SEQ ID NO: 10 (with terminal residues) and SEQ ID NO: 11 (without terminal residues)). The N- and C-termini of this peptide are histone tail clipping sites. The spectra also show existence of smaller fragments that contain combinations of PTM sites that are similar to the PTM combinations in the Thr22-Leu48 fragment.

Example 18

Detection of Histone Fragments Containing Citrulline

The normal and diseased pooled brain samples were digested with ArgC protease. The N-terminal portion of histone H3 contains several ArgC recognition sites including Arg2, Arg8, Arg17, Arg28 and Arg40, all of them being known PTM sites.

Figure 10A:
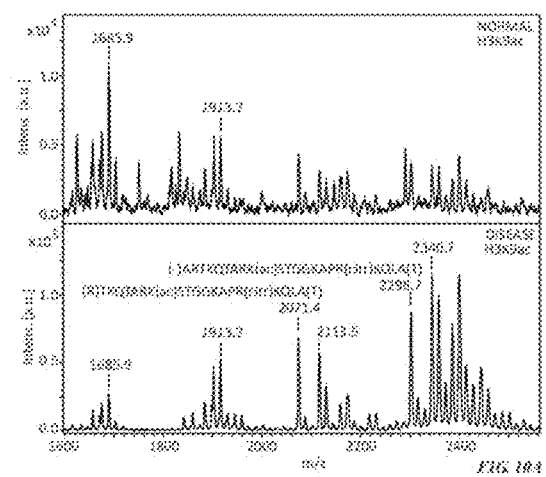
FIG. 10A shows linear mass spectra of normal and diseased brain samples obtained using ArgC digestion and H3K9ac enrichment in the 1600-2400 m/z mass region.

FIG. 10A shows mass spectra obtained from the normal and diseased samples using the H3K9ac antibody enrichment. The two spectra contain multiple matching peaks throughout the 1400-3200 m/z mass range, however the intensity of individual peaks in the diseased sample is 3- to 25-fold higher compared to the normal sample. The peaks form several groups: group 1 containing peaks in the 1600-1750 m/z mass range, group 2 containing peaks in the 1850-1950 m/z mass range, group 3 containing peaks in the 2050-2250 m/z mass range, group 4 containing peaks in the 2300-2600 m/z mass range.

Peaks in group 1 are assigned to Thr3-Arg17 fragments of histone H3 that are produced by ArgC-specific digestion and contain one missed cleavage (Arg8) and at least one PTM site (Lys9ac). For example, a peak at 1685.9 m/z is assigned to the Thr3-Arg17 fragment of histone H3 that contains 2 acetyl and 1 methyl group at Lys4, Lys9, Lys14: (R)TK(me)QTARK(ac)STGGK(ac)APR(K) (disclosed as SEQ ID NO: 12 (with terminal residues) and SEQ ID NO: 13 (without terminal residues)). There are 3 lysines in the Thr3-Arg17 sequence that are known PTM sites. Accordingly, at least 9 mass-resolved peaks are detected in this group that are assigned to combinations of acetylated and/or mono-, di- and tri-methylated lysines. In addition, pairs of peaks separated by approximately 18 m/z were detected and tentatively assigned to a dehydration (loss of water) that occurs at Thr3.

Peaks in group 2 have a pattern similar to group 1 and are assigned to larger Ala1-Arg17 fragments of histone H3 that are also produced by ArgC-specific digestion with 2 missed cleavages (Arg2 and Arg8). A larger number of peaks in this group is explained by the presence of an additional PTM site, Arg2.

Peaks in group 3 are assigned to histone H3 fragments that start at Thr3 and terminate at Ala21, Thr22 or Lys23 due to histone tail clipping. The peptides in this group contain 2 missed cleavages (Arg8 and Arg17) and several PTM sites including acetylated Lys9 that is recognized by the H3K9ac antibody. Certain peaks are assigned to fragments of histone H3 that contain deiminated arginine (citrulline). For example, the peak at 2071.4 m/z is assigned to the Thr3-

Ala21 fragment of histone H3 that contains citrullinated Arg17: (R)TKQTARK(ac)STGGKAPR(citr)KQLA(T) (disclosed as SEQ ID NO: 14 (with terminal residues) and SEQ ID NO: 15 (without terminal residues)). Citrullination causes the protease to skip over Arg17 thereby creating a missed cleavage site and increases a mass of the proteolytic peptide by 0.98 m/z that is detectable by MS. In this Example, the H3K9ac antibody specifically recognizes a fragment of histone H3 that contains acetylated Lys9 and non-modified (e.g. non-citrullinated) Arg8. A different antibody may be included in the bead array that specifically recognizes a fragment of histone H3 that contains both acetylated Lys9 and citrullinated Arg8. Such antibody may be used to enrich a different fraction of the histone H3 fragments from the sample.

Peaks in group 4 are assigned to histone H3 fragments that start at Ala1 and terminate at Ala21, Thr22 or Lys23. The peptides in this group contain 3 missed cleavages (Arg2, Arg8 and Arg17) and several sites that are acetylated, mono-, di- and tri-methylated. At least some of the missed cleavage sites, e.g. Arg2 and Arg17 contain modified residues, such as methylated and citrullinated arginine.

Figure 10B:
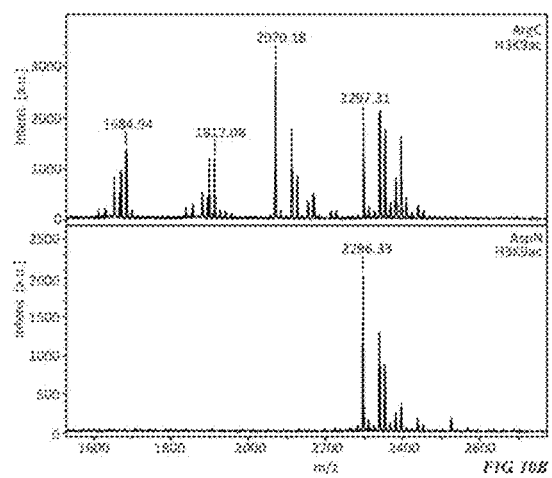
FIG. 10B shows reflector mass spectra of diseased brain samples obtained using ArgC and AspN digestions and H3K9ac enrichment in the 1600-2600 m/z mass region.
Figure 10C:
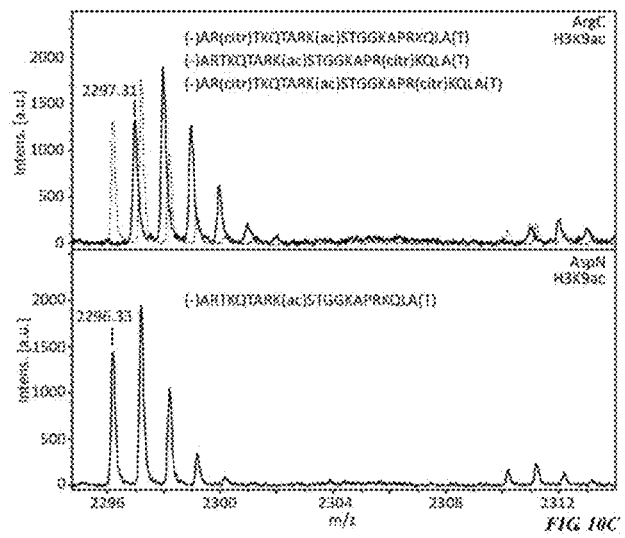
FIG. 10C shows reflector mass spectra of diseased brain samples obtained using ArgC and AspN digestion and H3K9ac enrichment in the 2296-2312 m/z mass region.

FIG. 10B shows that the pattern of peaks in the H3K9ac-enriched ArgC-digested diseased sample resembles the pattern of peaks in the H3K9ac-enriched AspN-digested diseased sample, yet the peptide fractions obtained from the corresponding samples are substantially different. For example, FIG. 10C shows that the 2296.33 m/z (mi) peak in the AspN-enriched fraction that is assigned to the Ala1-Ala21 fragment containing acetylated Lys9 is not present in the ArgC-enriched fraction. The latter instead contains a peak at 2297.31 m/z (mi) that is assigned to the Ala1-Ala21 fragment containing acetylated Lys9 and 1 citrullinated arginine. Furthermore, close examination of the isotope envelope of the 2297.31 peak shows different distribution of individual peaks compared to the isotope envelope of the 2296.33 peak. That is explained by the presence of fragments containing 1 and 2 citrullinated arginines in the ArgC-enriched fraction, e.g. citrullinated Arg2 and Arg17. The distribution of intensity within the isotope envelope of a peak is therefore a useful indicator of a number of citrullinated residues within a fragment of a histone.

The peptides in groups 3 and 4 are produced from clipped histone tails, while the peptides in groups 1 and 2 are produced from a mixture of clipped histone tails and intact histones. An evidence for the joint contribution of clipped histone tails and intact histones to the pool of peptides detected in groups 1 and 2 is found in the different spectral patterns observed for the corresponding peaks, such as different ratios of mono- to di-acetylated peptides in groups 1 and 3.

Similar to LysC digestion, digesting a histone-containing sample with ArgC may be used to select a fraction of a histone sequence that contains modified residues, Lys and Arg, respectively.

Example 19

Diagnostic Utility of Citrullinated Fragments of Histone H3

The H3K9ac enrichments of ArgC-digested normal and diseased samples produce spectra in which corresponding peaks have dramatically, e.g. greater than 10-fold, different intensities. Detection and quantification of histone fragments containing citrullinated and/or methylated arginine(s) may therefore be employed for detecting markers of a neurological disease in brain and other human and animal tissues.

Example 20

Detection of multiple fragments of an ion channel

The protein is voltage-dependent anion-selective channel protein 1 (VDAC1). The entry number and entry name for human VDAC1 in the UniProt database are P21796 and VDAC1 HUMAN, respectively. The antibody recognizing the N-terminus of VDAC1 was from Cell Signaling Technology, catalog #4866. Other manufacturers' antibodies that recognize the N-terminus of VDAC1 were also tested.

The sample is the previously described pooled non-Alzheimer's disease (control) human brain lysate digested with AspN protease (New England Biolabs, catalog #P8104S).

Figure 11:
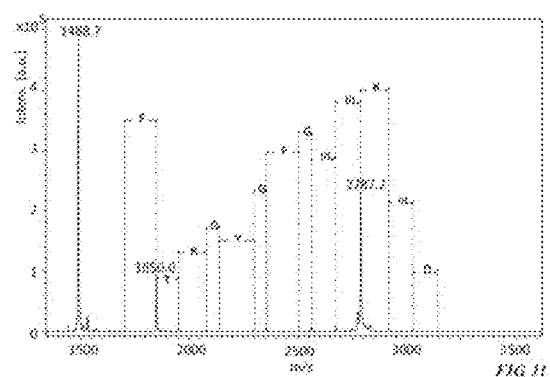
FIG. 11 shows a linear mass spectrum obtained by VDAC1 N-terminal fragment enrichment from AspN digested human brain lysate.

FIG. 11 shows proteolytic fragments of VDAC1 detected in a linear positive mode MALDI TOF mass spectrum recorded using VDAC1 N-terminus antibody enrichment. The peak at 1488.7 m/z is assigned by MS-MS sequencing to a peptide containing amino acids 2-15 of human VDAC1: (Ac)AVPPTYADLGKSAR (SEQ ID NO: 16), with 1 AspN missed cleavage (Ala8-Asp9), a C-terminus that is specifically cleaved by AspN, and an acetylated N-terminus. The peak at 1850.1 m/z is assigned to a peptide containing amino acids 2-18 of human VDAC1: (Ac)AVPPTYADLGKSARDVF (SEQ ID NO: 17), with 2 AspN missed cleavages, and an acetylated N-terminus. The peak at 2787.2 m/z is assigned to a peptide containing amino acids 2-27 of human VDAC1: (Ac)AVPPTYADLGKSARDVFTKGYGFGLI (SEQ ID NO: 18).

Multiple peaks are also detected between 1850 and 3100 m/z that are assigned to fragments of VDAC1 containing sequentially cleaved C-terminal amino acid residues, from Val17 to Asp30. These peaks have about 1-5% intensity of the 2787 peak. The peak intensities were used to determine relative abundance of the corresponding fragments in the sample.

Neither the Ala2-Ile27 peptide nor the peptides terminating at amino acids Lys20 through Asp30 were detected in a sample obtained from cultured mammalian MKN-45 cells. Table 1 lists relative abundances of various fragments of VDAC1 measured in pooled Alzheimer's Disease (AD), pooled non-diseased (control) human brain lysates and MKN-45 cell lysates, all digested with AspN protease. The relative abundances of individual fragments were calculated using intensities of the corresponding peaks in the mass spectra.

TABLE 1 relative abundances of VDAC-1 fragments in various samples

| Protein fragment, MW (average) | Relative abundance in AD brain (%) | Relative abundance in control brain (%) | Relative abundance in MKN-45 (%) |
|---|---|---|---|
| Ala2-Arg15, 1488.7 | 100 | 100 | 100 |
| Ala2-Phe18, 1850.1 | 25 | 20 | 5 |
| Ala2-Lys20, 2079.4 | 1.0 | 0.9 | below 0.1 |
| Ala2-Gly21, 2136.4 | 0.4 | 0.4 | below 0.1 |
| Ala2-Tyr22, 2299.6 | 0.6 | 0.9 | below 0.1 |
| Ala2-Gly23, 2356.7 | 1.2 | 1.6 | below 0.1 |
| Ala2-Phe24, 2503.8 | 1.0 | 1.7 | below 0.1 |
| Ala2-Gly25, 2560.9 | 1.0 | 2.0 | below 0.1 |

TABLE 1-continued relative abundances of VDAC-1 fragments in various samples

| Protein fragment, MW (average) | Relative abundance in AD brain (%) | Relative abundance in control brain (%) | Relative abundance in MKN-45 (%) |
|---|---|---|---|
| Ala2-Leu26, 2674.0 | 1.3 | 1.3 | below 0.1 |
| Ala2-Ile27, 2787.2 | 96 | 50 | below 0.1 |

The above-described immunoassay method may be used for characterizing two or a greater number of biological samples by using the following steps: (1) detecting in each sample a peptide ladder, that is a group containing at least 3 fragments of a protein, each of the fragments having a different sequence length than other fragments in the group, each of the fragments differing from another fragment in the group by a single terminal amino acid residue, and (2) obtaining an estimate of relative abundance of each fragment in each sample. In this method, each of the fragments contains an epitope that is recognized by a specific capture agent, e.g. an antibody. The sample may be prepared by digestion using an external protease such that each of the fragments contains an N- or a C-terminus that is cleaved by a protease that is distinct from the external protease.

Example 21

Detection of Multiple Fragments of Transcription Factor TFAM

The protein is transcription factor A, mitochondrial (TFAM). The entry number and entry name in the UniProt database are Q00059 and TFAM_HUMAN, respectively. The antibody that recognizes the N-terminal region of TFAM was from Cell Signaling Technology, catalog #7495. Other manufacturers' antibodies that recognize the N-terminal region of TFAM containing the high mobility group (HMG) box 1 domain were also tested. The tested antibodies recognized sequence YLRFSKEQLPI (SEQ ID NO: 19) corresponding to amino acids 57-67 of human TFAM.

The sample is the previously described pooled non-Alzheimer's disease (control) human brain lysate digested with AspN protease.

Multiple peaks were detected in the mass spectra between 1200-7000 m/z that were assigned to fragments of TFAM produced by an endogenous protease (mitochondrial Lon protease). The peaks were assigned to the following TFAM fragments: Ser56-Ile67, Ser55-Ile67, Ser55-Lys69, Ser55-Ala70, Val54-Ala70, Cys49-Ile67, Ser48-Ile67, Ala47-Ile67, Leu46-Ile67, Val45-Ile67, Ser44-Ile67, Ser43-Ile67, Ser55-Ile81, Ser43-Thr78, Ser43-Leu80, Ser43-Ile81, Ser55-Gln100, Ser43-Gln100. The C-termini of the last two fragments are specifically cleaved by AspN protease (Gln100-Asp101). Ser43 is the first amino acid in the sequence of mature TFAM, which is produced by removal of the transit peptide 1-42.

Example 22

Detection of C-Terminal Fragments of Enzyme ACLY

The protein is ATP-citrate synthase (ACLY). The UniProt database entry number and entry name for human ACLY are P53396 and ACLY_HUMAN, respectively. The antibody that recognizes the C-terminus of ACLY was from Abcam (Cambridge Mass.), catalog #ab40793.

The sample is the previously described pooled non-Alzheimer's disease (control) human brain lysate digested with ArgC protease.

Several peaks were detected in the mass spectra that were assigned to fragments of ACLY as follows. A peak at 1958.2 m/z (average) was assigned to the C-terminal ACLY fragment containing amino acid residues His1086-Met1101: HPWDDISYVLPEHMSM (SEQ ID NO: 20). Peaks at 1974.2, 1990.2, 2006.2 and 2022.2 m/z (average) were assigned to the ACLY fragments 1086-1101 containing 1, 2, 3 and 4 oxidized amino acid residues, respectively. Based on MS-MS sequencing of the 2022.2 m/z fragment, the oxidized residues were Trp1088, His1098, Met1099 and Met1101.

In addition, peaks were detected at lower m/z values that were assigned as follows: 1827.0 m/z: fragment His1086-Ser1100, 1739.9 m/z: fragment His1086-Met1099, 1608.8 m/z: fragment His1086-His1098, 1471.6 m/z: fragment His1086-Glu1097.

The above-described method may be used for detecting and measuring the extent of oxidative stress in a biological sample by analyzing intensities of C-terminal fragments of ACLY containing 1, 2, 3 or 4 oxidized amino acid residues (Met. His, Trp).

Example 23

Tail Clipping in Histone H4

The previously described LysC-digested human brain samples were separately probed with an antibody specific for acetylated histone H4. The antibody was from Abcam (catalog #ab240201, anti-histone H4 (acetyl K5+K8+K12+K16)). The analysis of mass spectra revealed several peaks that were assigned to fragments of human histone H4. A peak at 1583.8 m/z (average) was assigned to a fragment Ser1-Lys16 containing 3 acetylated lysines (Lys5, Lys8, Lys12), 1 non-modified lysine (Lys16) and an acetylated N-terminus. A peak at 2203.5 m/z (average) was assigned to a fragment Ser1-Lys20 containing 4 acetylated lysines (Lys5, Lys8, Lys12, Lys16), 1 non-modified lysine (Lys20) and an acetylated N-terminus. A peak at 2443.9 m/z (average) was assigned to a fragment Ser1-Leu22 containing 4 acetylated lysines (Lys5, Lys8, Lys12, Lys16), 1 di-methylated lysine (Lys20), an acetylated N-terminus and terminating at a tail clipping site leucine 22. A nearby peak at 2429.9 m/z (average) was assigned to the Ser1-Leu22 fragment containing mono-methylated Lys20. A peak at 2942.4 m/z (average) was assigned to a fragment Ser1-Ile26 containing 4 acetylated lysines (Lys5, Lys8, Lys12, Lys16), 1 di-methylated lysine (Lys20), an acetylated N-terminus and terminating at a tail clipping site isoleucine 26. A nearby peak at 2928.4 m/z (average) was assigned to the Ser1-Ile26 fragment containing mono-methylated Lys20. A peak at 3240.8 m/z (average) was assigned to a fragment Ser1-Ile29 containing 4 acetylated lysines (Lys5, Lys8, Lys12, Lys16), 1 di-methylated lysine (Lys20), acetylated N-terminus and terminating at a tail clipping site isoleucine 29. This Example shows detection of histone H4 fragments cleaved at their respective C-termini by an endogenous protease and terminating at tail clipping sites Leu22, Ile26 and Ile29. Note that the numbering of human histone H4 sequence typically starts at Ser1, as the N-terminal methionine is removed.

Example 24

Using a Bead Array in the Discovery Mode

Analysis of samples containing fragments of histone H3 was performed without prior knowledge of which sequences may be captured by the antibodies included in the bead array. One example is the detection of multiple fragments of histone H3 that terminate at novel histone tail cleavage sites located past residue Thr32. The experimental data shows that a combination of immunoaffinity enrichment and MS analysis may be used to discover novel fragments in histone H3 and other histones in various biological samples.

All patents, patent applications, and published references cited herein are hereby incorporated by reference in their entirety. While the present disclosure has been described in connection with the specific embodiments thereof, it will be understood that it is capable of further modification. Furthermore, this application is intended to cover any variations, uses, or adaptations of the disclosure, including such departures from the present disclosure as come within known or customary practice in the art to which the disclosure pertains, and as fall within the scope of the appended claims.

REFERENCES

Liu H. et al, "Clipping of arginine-methylated histone tails by JMJD5 and JMJD7" Proc. Natl. Acad. Sci. USA. 2017 Sep. 12; 114(37): E7717-E7726. Epub 2017 Aug. 28.

---

What is claimed is:

1. A method for characterizing a proteolytic cleavage status of a naturally occurring protein in a biological material, the method comprising the steps of:
   obtaining a sample produced by digesting a biological material using an external protease, the sample containing a first peptide and a second peptide, the first and the second peptides being distinct fragments of a naturally occurring protein, the first peptide containing both an N-terminus and a C-terminus cleaved by an endogenous protease, the second peptide containing both an N-terminus and a C-terminus cleaved by the external protease,
   providing a reactive site, the reactive site comprising a bead and a capture agent associated with the bead,
   causing the first and the second peptides to specifically bind to the same reactive site,
   individually analyzing the reactive site to obtain a mass spectrum that contains a signal from the first peptide and a signal from the second peptide,
   detecting relative abundances of the first peptide and the second peptide by analyzing the signal from the first peptide and the signal from the second peptide, and
   correlating the relative abundances of the first peptide and the second peptide with a proteolytic cleavage status of the naturally occurring protein in the biological material.

2. The method of claim 1 wherein the naturally occurring protein is one of an ion channel, a transcription factor and a histone.

3. The method of claim 1 wherein the first peptide further contains a cleavage site recognized by the external protease.

4. The method of claim 1 wherein the first peptide is derived from a clipped tail of a histone and the second peptide is derived in part from the clipped tail of a histone.

5. The method of claim 1 wherein the first peptide is derived from a clipped tail of a histone and the second peptide is derived from a non-clipped histone.

6. The method of claim 1 wherein the first peptide signal is separated by at least 10 m/z units from the second peptide signal.

7. The method of claim 1 wherein the first peptide signal and the second peptide signal are detected in a region of the mass spectrum that spans at least 100 m/z units and is substantially free of signals from peptides cleaved by the external protease.

8. The method of claim 1 wherein each of the first and the second peptides contains an amino acid sequence of human histone H3 starting at one of Ala1, Arg2, Thr3, Lys4, Gln5 and terminating at one of Ala21, Thr22, Lys23, Ala24, Ala25, Arg26, Lys27, Ser28, Ala29.

9. The method of claim 1 wherein each of the first and the second peptides contains an amino acid sequence of human histone H3 starting at one of Ala1, Thr22, Lys23, Ala24, Ala25, Arg26, Lys27, Ser28, Ala29 and terminating at one of Val46, Ala47, Leu48.

* * * * *